(12) United States Patent
Dalko et al.

(10) Patent No.: US 8,741,272 B2
(45) Date of Patent: Jun. 3, 2014

(54) USE OF NOVEL AMINO ACID DERIVATIVES AS AGENTS FOR TREATING HUMAN PERSPIRATION, AND COMPOSITIONS CONTAINING THEM

(75) Inventors: Maria Dalko, Versailles (FR); Julien Hitce, Fontenay Aux Rose (FR); Thomas Delanne, Paris (FR)

(73) Assignee: L'Oreal, Paris (FR)

( * ) Notice: Subject to any disclaimer, the term of this patent is extended or adjusted under 35 U.S.C. 154(b) by 4 days.

(21) Appl. No.: 13/704,454

(22) PCT Filed: Jun. 8, 2011

(86) PCT No.: PCT/EP2011/059531
§ 371 (c)(1),
(2), (4) Date: Feb. 27, 2013

(87) PCT Pub. No.: WO2011/157610
PCT Pub. Date: Dec. 22, 2011

(65) Prior Publication Data
US 2013/0164237 A1    Jun. 27, 2013

Related U.S. Application Data

(60) Provisional application No. 61/357,392, filed on Jun. 22, 2010.

(30) Foreign Application Priority Data

Jun. 17, 2010 (FR) ...................... 10 54800

(51) Int. Cl.
*C07K 7/02* (2006.01)
*A61K 8/64* (2006.01)
*A61Q 15/00* (2006.01)
*C07K 7/06* (2006.01)

(52) U.S. Cl.
CPC . *C07K 7/02* (2013.01); *A61Q 15/00* (2013.01); *C07K 7/06* (2013.01); *A61K 8/64* (2013.01)
USPC .............................. 424/65; 530/328; 530/329

(58) Field of Classification Search
None
See application file for complete search history.

(56) References Cited

FOREIGN PATENT DOCUMENTS

WO    WO 2010/009892    *    1/2010

* cited by examiner

*Primary Examiner* — Bethany Barham
*Assistant Examiner* — Danah Al-Awadi
(74) *Attorney, Agent, or Firm* — Novak Druce Connolly Bove + Quigg LLP

(57) ABSTRACT

The invention relates to the use, as an agent for treating human perspiration, in a cosmetic composition, of amino acid derivatives of formula (I) below:

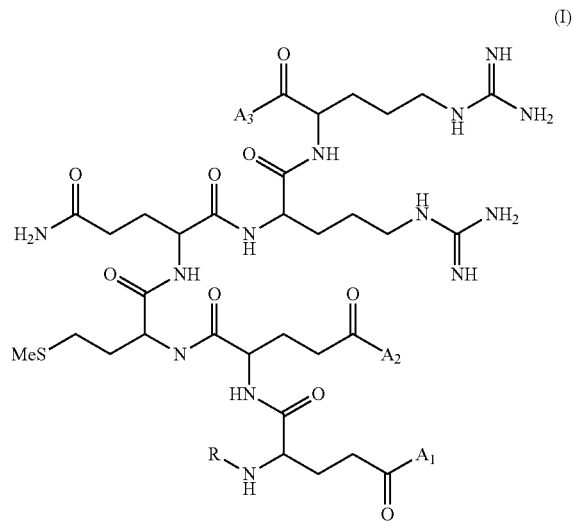

The invention also relates to a cosmetic process for treating perspiration and possibly the body odour associated with human perspiration, especially underarm odour. The invention also relates to novel amino acid derivatives of formula (II) that will be defined in detail hereinbelow, and to cosmetic or dermatological compositions containing them.

20 Claims, No Drawings

USE OF NOVEL AMINO ACID DERIVATIVES AS AGENTS FOR TREATING HUMAN PERSPIRATION, AND COMPOSITIONS CONTAINING THEM

CROSS REFERENCE TO RELATED APPLICATIONS

This application is a National Phase filing under 35 U.S.C. §371 of PCT/EP2011/059531 filed on Jun. 8, 2011; and this application claims priority to Application No. 1054800 filed in France on Jun. 17, 2010 under 35 U.S.C. §119; and this application claims the benefit of U.S. Provisional Application No. 61/357,392 filed on June 22, 2010; the entire contents of all are hereby incorporated by reference.

The invention relates to the use, as an agent for treating human perspiration, in a cosmetic composition, of amino acid derivatives of formula (I) that will be defined in detail hereinbelow.

The invention also relates to a cosmetic process for treating perspiration and possibly the body odour associated with human perspiration, especially underarm odour.

The invention also relates to novel amino acid derivatives of formula (II) that will be defined in detail hereinbelow, and to cosmetic or dermatological compositions containing them.

In the cosmetics field, it is well known to use in topical application, as antiperspirants, aluminium and/or zirconium salts, which have the effect of limiting or even preventing the flow of sweat. These products are generally available in the form of roll-ons, sticks, aerosols or sprays.

Metal salts of this type are efficient as antiperspirant active agents, but some people find that the application of such products causes skin irritation. Moreover, aluminium salts partly block perspiration via the formation of a partial plug in the sweat duct, giving the consumer the impression of unnatural control of perspiration. Furthermore, they also have a tendency to leave marks on clothing.

Patent application WO 2006/094 193 (Revance Therapeutics) discloses oligopeptides comprising a sequence Glu.Glu.Met.Gln.Arg.Arg, which are intended to be applied transdermally for a multitude of treatments, including the treatment of hyperhydrosis.

Research Disclosure Vol. 519, 07 2007, p. 685, discloses the peptide ß-Ala-Pro-diaminobutyroylbenzylamide, such as the product sold by the company Pentapharm AG, which is used in the treatment of hyperhydrosis.

It has been proposed in patent application WO 2010/003 781, for the treatment of perspiration, to use peptides in lamellar-phase emulsions, especially oleosomes. Among the recommended peptides, the said document mentions peptides comprising a sequence Glu.Glu.Met.Gln.Arg.Arg, peptides comprising a sequence Tyr.Ala.Gly.Phe.Leu, and the peptide β-Ala-Pro-diaminobutyroylbenzylamide.

These peptides are not entirely satisfactory for the treatment of human perspiration.

There is thus still a need to find novel formulations for treating perspiration that do not have the drawbacks encountered with those known hitherto, and which give good antiperspirant efficacy. There is thus a need to find novel antiperspirant active agents that can replace aluminium salts and aluminium/zirconium salts, and that are efficient, easy to formulate and well tolerated.

The Applicant has found, surprisingly, that amino acid derivatives of formula (I) that will be given in detail hereinbelow make it possible to achieve this objective and can be readily formulated in numerous products for reducing perspiration, without it being necessary to use standard astringent salts.

A subject of the invention is also the use of at least one amino acid derivative of formula (I) that will be given in detail hereinbelow, as an agent for treating human perspiration, in a composition comprising a cosmetically acceptable support.

The invention relates to the use, as an agent for treating human perspiration, in a cosmetic composition, of amino acid derivatives of formula (I) that will be defined in detail hereinbelow.

A subject of the present invention is also a cosmetic process for treating human perspiration and optionally body odour, in particular underarm odour, which consists in applying to the surface of the skin a composition comprising, in a cosmetically acceptable medium, at least one amino acid derivative of formula (I) that will be given in detail hereinbelow.

The invention also relates to novel amino acid derivatives of formula (II) that will be defined in detail hereinbelow, and to cosmetic or dermatological compositions containing them.

The term "cosmetically acceptable" means compatible with the skin and/or its integuments, having a pleasant colour, odour and feel and not causing any unacceptable discomfort (stinging, tautness or redness) liable to discourage the consumer from using this composition.

The term "agent for treating perspiration" means any substance which has the effect of reducing the flow of sweat and/or of reducing the sensation of moisture associated with human sweat, and/or of masking human sweat.

Amino Acid Derivatives

The amino acid derivatives in accordance with the invention are chosen from those corresponding to formula (I) below, or a salt thereof, optical isomers, stereoisomers, enantiomers and diastereoisomers thereof, or a geometrical isomer thereof:

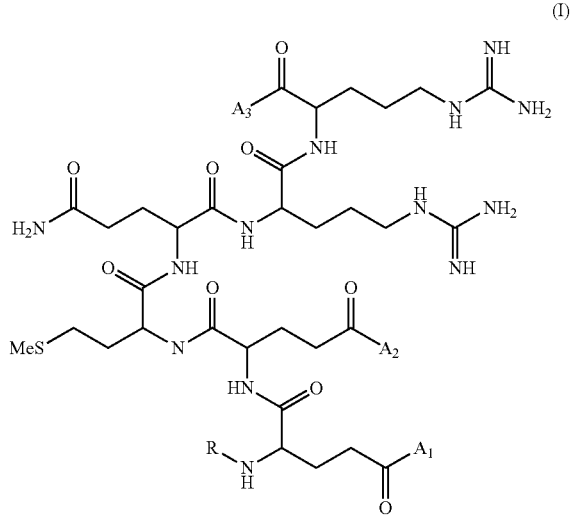

(I)

in which:

$A_1$ and $A_2$ independently denote a radical chosen from:
a) —$OR_3$ with $R_3$ denoting a hydrogen atom or a linear or branched, saturated or unsaturated $C_1$-$C_{18}$ alkyl radical;
b) —NH—$(CH_2)_m$—$CO_2H$ with m=0, 1, 2, 3 or 4,
c) $NR_1R_2$ with $R_1$ and $R_2$, which may be identical or different, denoting hydrogen or a linear or branched, saturated or unsaturated $C_1$-$C_{12}$ alkyl radical;

d) a group chosen from

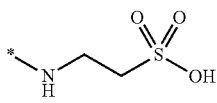
(taurine)

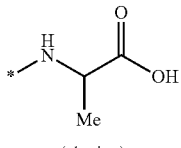
(alanine)

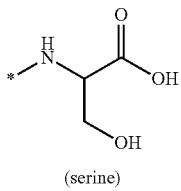
(serine)

$A_3$ denotes a group chosen from:

(i) $NR_4R_5$ with $R_4$ and $R_5$, which may be identical or different, denoting hydrogen or a linear or branched, saturated or unsaturated $C_1$-$C_{18}$ alkyl radical;

(ii) —$OR'_1$ with $R'_1$ denoting a hydrogen atom or a linear or branched, saturated or unsaturated $C_1$-$C_{18}$ alkyl radical;

(iii) aralkyl such as benzyl (iv) —NH—$(CH_2)_m$—$CO_2H$ with m=0, 1, 2, 3 or 4 or alternatively (v) a radical chosen from

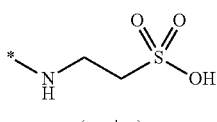
(taurine)

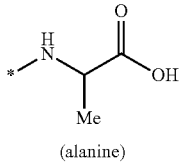
(alanine)

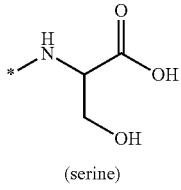
(serine)

R denotes a radical chosen from:

1) saturated or unsaturated $C_2$-$C_{18}$ acyl, such as acetyl
2) aryl, in particular phenyl
3) aralkyl such as benzyl
4) linear or branched, saturated or unsaturated $C_1$-$C_{12}$ alkyl 5) a group chosen from the following groups:

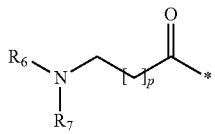
with p = 0, 1, 2, 3

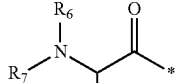

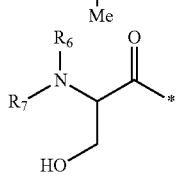

in which $R_6$ and $R_7$, which may be identical or different, denote a hydrogen atom; a linear or branched, saturated or unsaturated $C_1$-$C_{18}$ alkyl radical; a linear or branched, saturated or unsaturated $C_2$-$C_{18}$ acyl radical such as acetyl;

with the exception of compound (a) of structure:

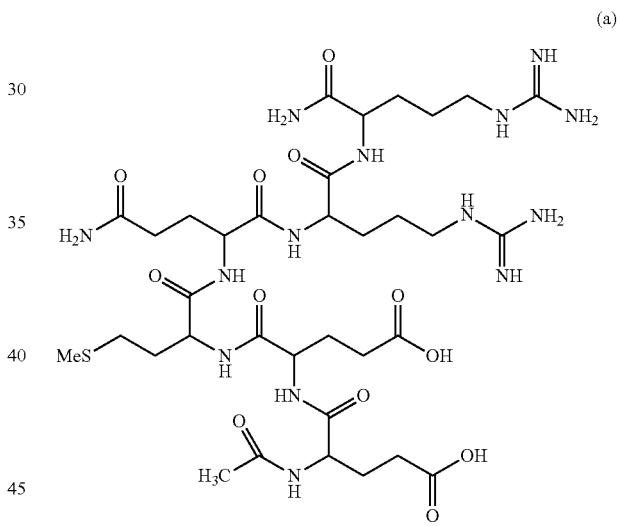

(a)

In formula (I) or (II), among the alkyl groups, mention may be made especially of methyl, ethyl, n-propyl, isopropyl, n-butyl, isobutyl, tert-butyl, n-octyl, 2-ethylhexyl, dodecyl and hexadecyl groups.

The acceptable salts of the compounds described in the present invention include conventional non-toxic salts of the said compounds, such as those formed from organic or mineral acids. Examples that may be mentioned include the salts of mineral acids, such as sulfuric acid, hydrochloric acid, hydrobromic acid or phosphoric acid. Mention may also be made of the salts of organic acids, which may comprise one or more carboxylic, sulfonic or phosphonic acid groups. They may be linear, branched or cyclic aliphatic acids, or alternatively aromatic acids. These acids may also include one or more heteroatoms chosen from O and N, for example in the form of hydroxyl groups. Mention may be made especially of propionic acid, acetic acid, terephthalic acid, citric acid, tartaric acid and lactic acid.

The salts of organic or mineral bases such as the ammonium salts, the alkanolamine salts such as those of triethanolamine or of aminopropanediol, and the salts of alkali metals such as sodium or potassium, or of calcium.

The preferred salts are those obtained from hydrochloric acid, sulfuric acid, acetic acid, tartaric acid, citric acid and lactic acid.

A first family of preferential compounds of formula (I) is constituted by those for which $A_1$ denotes a radical OH.

Even more preferably, according to this same variant:

$A_2$ denotes a radical —NH—$(CH_2)_m$—$CO_2H$, $A_3$ denotes a radical chosen from:

(i) $NR_4R_5$ or (iii) —NH—$(CH_2)_m$—$CO_2H$.

R denotes a radical chosen from:

1) saturated or unsaturated $C_2$-$C_6$ acyl, such as acetyl
2) linear or branched, saturated or unsaturated $C_1$-$C_{16}$ alkyl
3) a group

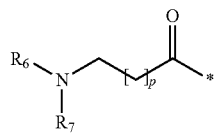

Even more preferably, according to this first variant, R denotes an acetyl radical, $A_3$ denotes a radical $NH_2$, $A_1$ denotes a hydroxyl radical (—OH) and $A_2$ denotes a radical —NH—$(CH_2)_m$—$CO_2H$.

Another family of preferential compounds of formula (I) is constituted by those for which:

$A_1$ denotes a radical —NH—$(CH_2)_m$—$CO_2H$, or a group chosen from

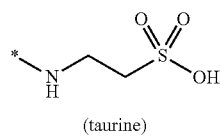
(taurine)

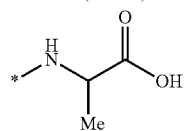
(alanine)

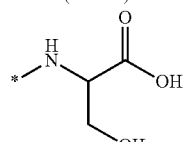
(serine)

$A_2$ denotes —$OR_3$, a radical —NH—$(CH_2)_m$—$CO_2H$, or a radical chosen from

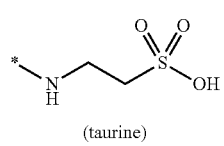
(taurine)

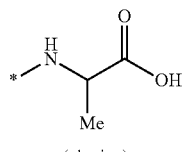
(alanine)

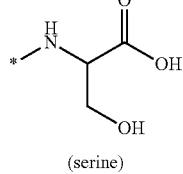
(serine)

$A_3$ denotes a radical chosen from:

(i) $NR_4R_5$ or (ii) —NH—$(CH_2)_m$—$CO_2H$ (iii) a radical chosen from

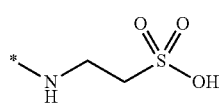
(taurine)

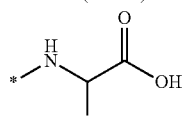
(alanine)

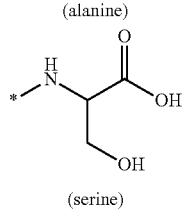
(serine)

According to this second variant, preferably:

$A_1$ denotes a radical —NH—$(CH_2)_m$—$CO_2H$ and $A_2$ denotes a radical —NH—$(CH_2)_m$—$CO_2H$, or a group OH $A_3$ denotes a group chosen from:

(i) $NR_4R_5$ with $R_1$ and $R_2$, which may be identical or different, denoting hydrogen or a linear or branched, saturated or unsaturated $C_1$-$C_{12}$ alkyl radical;

(ii) —NH—$(CH_2)_m$—$CO_2H$

R denotes a radical chosen from saturated or unsaturated $C_2$-$C_{18}$ acyl, such as acetyl, or alternatively a group

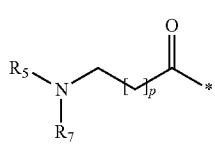

Even more preferably:

R denotes an acetyl radical, $A_3$ denotes a radical $NH_2$, $A_1$ denotes a radical —NH—$(CH_2)m$—$CO_2H$ and $A_2$ denotes a radical —NH—$(CH_2)m$—$CO_2H$ or a hydroxyl radical (—OH).

Among the amino acid derivatives in accordance with the invention, use will be made more particularly of those chosen from the following compounds, or a salt thereof, optical isomers, stereoisomers, enantiomers and diastereoisomers thereof, or a geometrical isomer thereof:

Compound 1

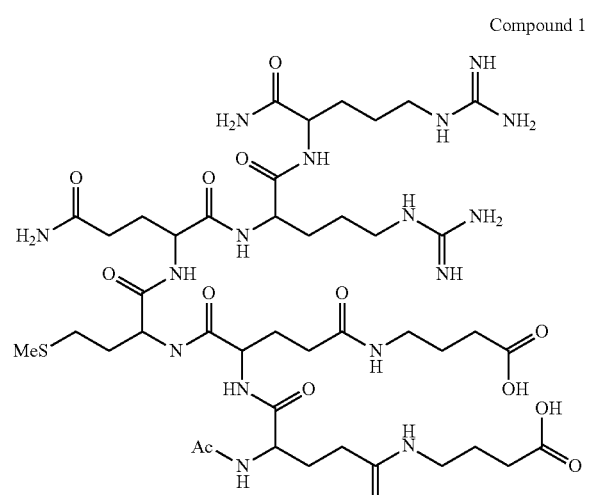

Compound 2

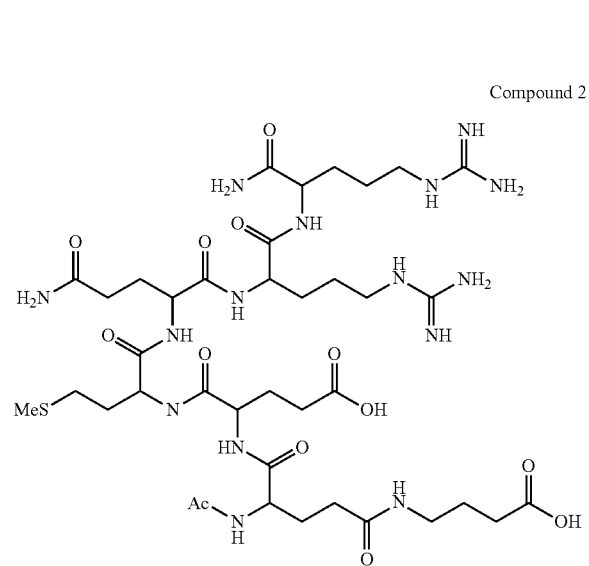

Compound 3

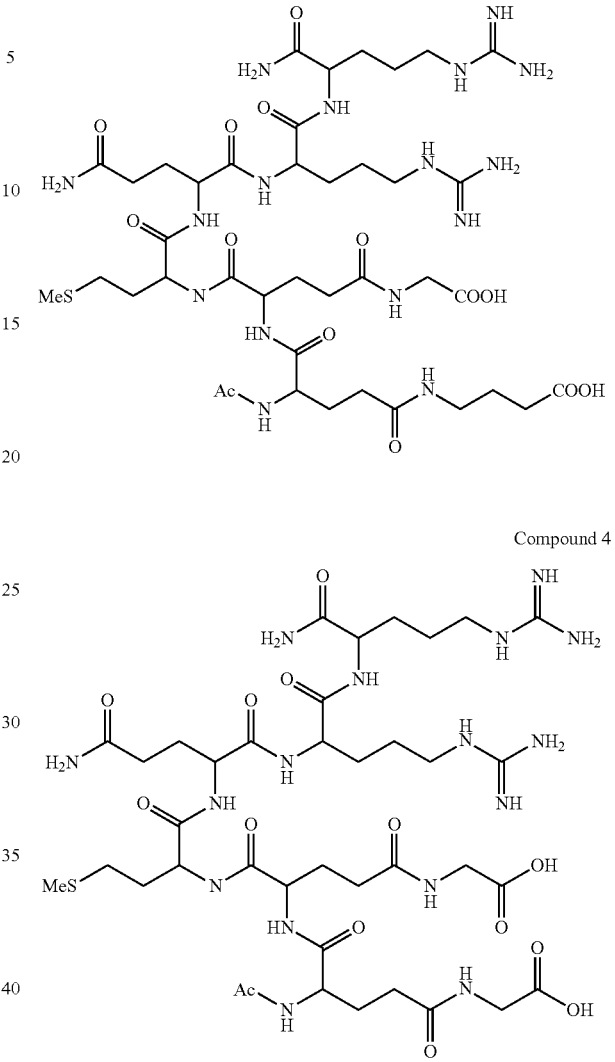

Compound 4

Compound 5

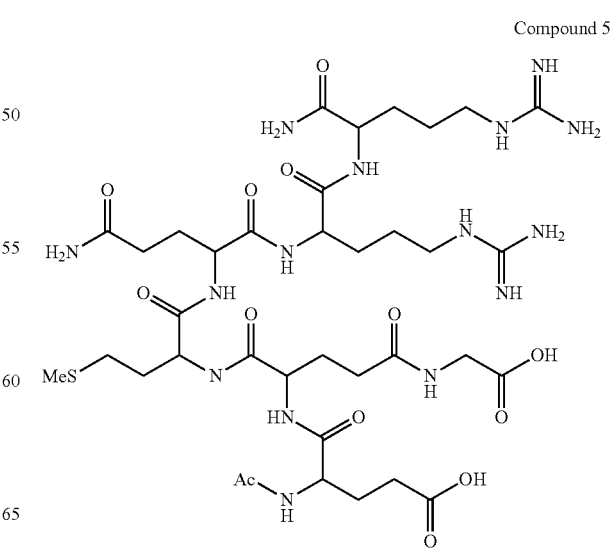

Compound 6

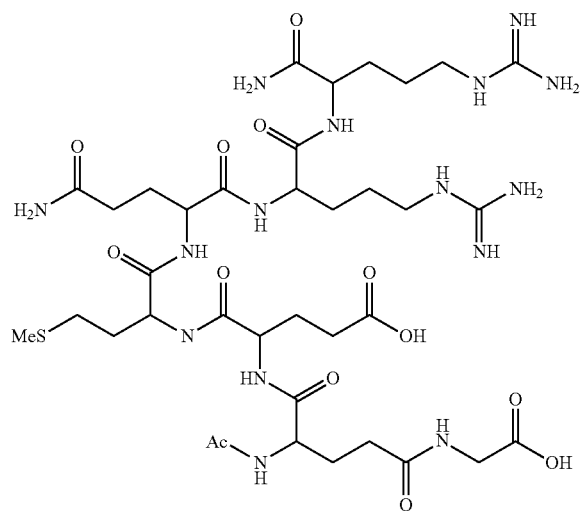

The amino acid derivatives of formula (I) according to the present invention are peptides that may be of natural origin or may be synthesized without difficulty by a person skilled in the art, using the conventional techniques of solid-phase or solution peptide synthesis (M. Bodanszky, Principles of Peptides Synthesis, 2nd Ed., 1993, Edition Springer-Verlag).

To prepare the compounds of formula (I) as a solution and/or salts thereof, several synthetic routes may be envisaged. For example, the peptide part may be constructed linearly from the N-terminal end to the C-terminal end or, conversely, from the C-terminal end to the N-terminal end. More specifically, the peptide chain may be synthesized by reacting an N-protected amino acid with a C-protected amino acid to generate an N- and C-protected dipeptide, which may itself lead to a tripeptide after deprotection of its N-terminal end and reaction of the NH$_2$ function thus released with an N-protected amino acid, or after deprotection of its C-terminal end and reaction of the COOH function thus released with a C-protected amino acid. This principle is repeated as many times as necessary to obtain the desired peptide sequence.

The reaction between two amino acids that are N- and C-protected, respectively, may necessitate the use of an activation step and the employment of a coupling reagent. The standard activation or coupling reagents in peptide synthesis are, for example, carbodiimides such as DCC (=dicyclohexylcarbodiimide) or the water-soluble forms of carbodiimides such as EDC (=N-ethyl-N'-(3-dimethylaminopropyl)carbodiimide hydrochloride), phosphonium salts such as BOP (=benzotriazol-1-yloxy) tris(dimethylamino)phosphonium hexafluorophosphate), PyBOP (=(benzotriazol-1-yloxy) tripyrrolidinophosphonium hexafluorophosphate), PyBROP (=bromotripyrrolidinophosphonium hexafluorophosphate), PyCloP (=chlorotripyrrolidinophosphonium hexafluorophosphate), or reagents such as PyClU (=chloro-N,N,N',N'-bis(tetramethylene) formamidinium hexafluorophosphate), N-hydroxysuccinimide, EEDQ (=1-ethoxycarbonyl-2-ethoxy-1,2-dihydroquinoline), CDI (=carbonyldiimidazole), or chloroformates such as ethyl chloroformate or isobutyl chloroformate. When the coupling is performed using coupling reagents such as carbodiimides, additives such as HOBt (=1-hydroxybenzotriazole) or N-hydroxysuccinimide may be added during the reaction to limit the racemization.

The protecting groups for amine functions are, for example:
Adoc=1-adamantyloxycarbonyl
Boc=t-butyloxycarbonyl
2-bromo-Z=2-bromobenzyloxycarbonyl
2-chloro-Z=2-chlorobenzyloxycarbonyl
Fmoc=9-fluorenylmethoxycarbonyl
Formyl
Nicotinoyl
TFA=trifluoroacetyl
Tos=p-toluenesulfonyl
The protecting groups for acid functions are, for example: methyl; ethyl; benzyl; i-propyl; t-butyl esters
The protecting groups for the guanidine function of the arginine residues are, for example:
N,N'-di(Adoc)
N,N'-di(Boc)
By way of illustration, the following scheme describes the case where the peptide chain is constructed according to this principle from the N-terminal end to the C-terminal end.

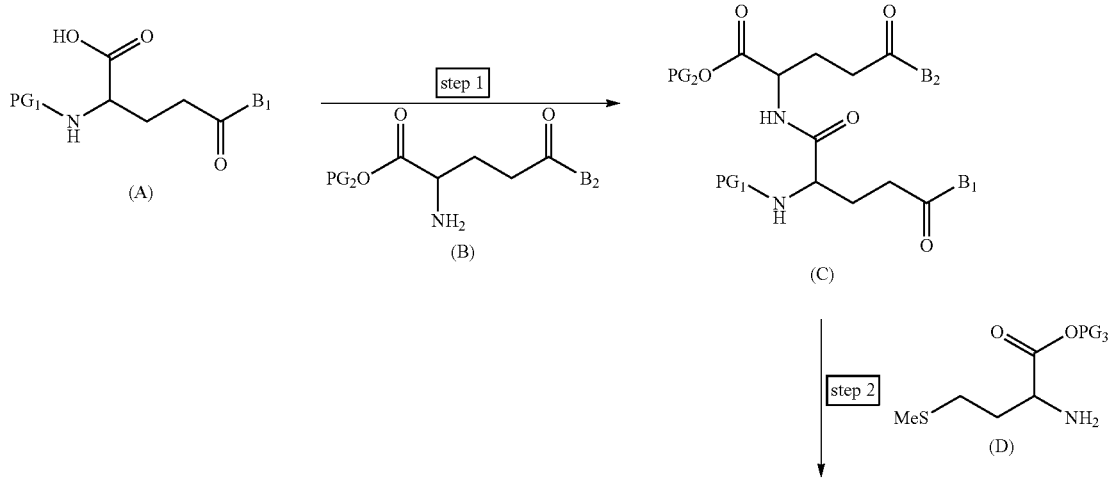

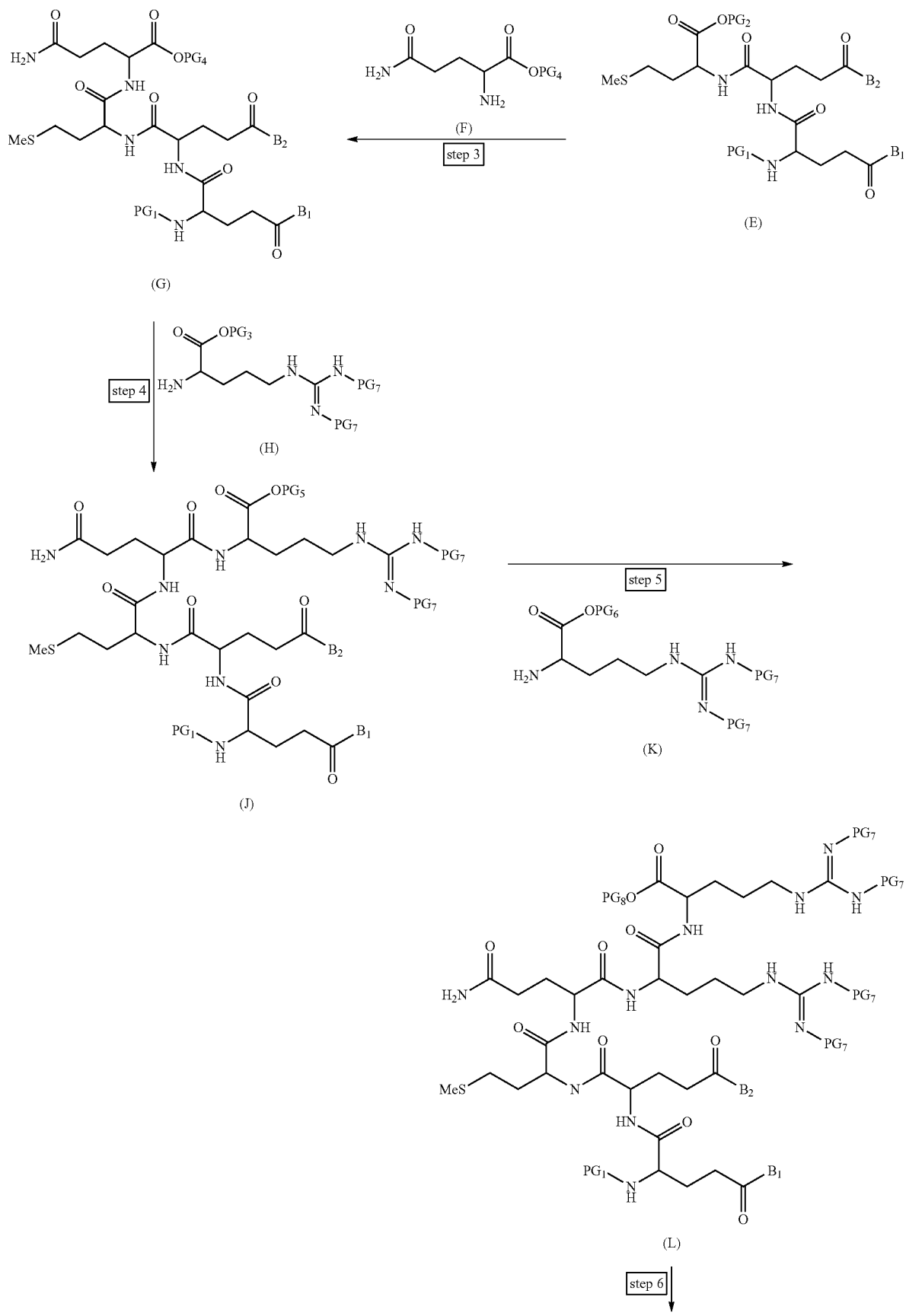

-continued

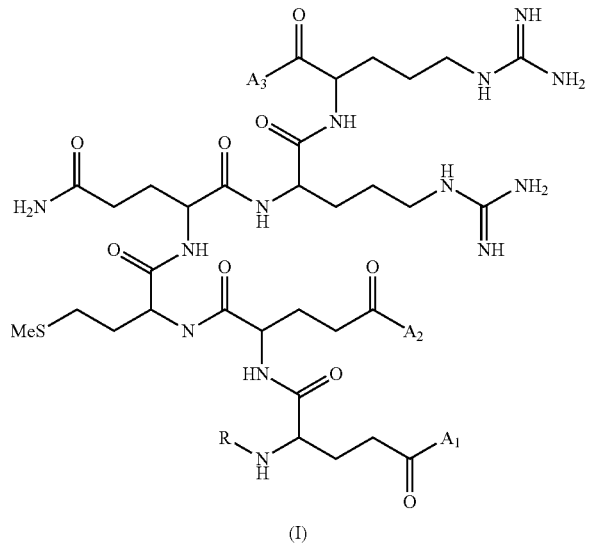

(I)

PG$_1$ denotes an amine-function protecting group or R

PG$_2$, PG$_3$, PG$_4$, PG$_5$, PG$_6$ independently denote a carboxylic acid-function protecting group PG$_7$ denotes a group for protecting the guanidine function of arginine.

B$_1$ and B$_2$ independently denote, respectively, a radical A$_1$ and A$_2$ or a precursor of radical A$_1$ or of A$_2$, respectively, as indicated in the text hereinbelow.

In step 1, the glutamic acid derivative (A), N-substituted with a group PG$_1$, is coupled to the C-protected glutamic acid derivative (B) to give the N- and C-substituted dipeptide (C). In step 2, after deprotection of the C-terminal end of (C), the compound obtained is coupled to a C-protected methionine residue (D) to give the N- and C-substituted tripeptide (E). In step 3, after deprotection of the C-terminal end of (E), the compound obtained is coupled to a C-protected glutamine residue (F) to give the N- and C-substituted tetrapeptide (G). In step 4, after deprotection of the C-terminal end of (G), the compound obtained is coupled to a C- and N,N'-protected arginine residue (H) to give the pentapeptide (J). In step 5, after deprotection of the C-terminal end of (J), the compound obtained is coupled to a C- and N,N'-protected arginine residue to give the hexapeptide (L).

Step 6 includes a sequential deprotection of the protecting groups, where appropriate. Depending on its nature, the protecting group PG$_1$ of the peptide derivative (L) may be converted into the substituent R in step 6 as represented above, but also further upstream in the course of the synthesis. It is thus possible, for example, to have R=PG$_1$.

Similarly, depending on the nature of A$_1$ and/or A$_2$, the radicals A$_1$ and/or A$_2$, respectively, may be introduced from B$_1$ and/or B$_2$, respectively, at the end of the reaction scheme on to the desired terminated peptide sequence or further upstream in the course of the reaction scheme. It is thus possible to have, for example, A$_1$=B$_1$ and/or A$_2$=B$_2$. In the case where B$_1$ and/or B$_2$ are derived from amino acids, these substituents may be introduced by coupling between the carboxylic acid function of the glutamic acid residues and the amine function of the appropriate C-protected amino acid under the conditions of a peptide coupling. This functionalization of the side chains of the glutamic acid residues may be performed before the assembly of the hexapeptide chain, during this assembly or at the end of the reaction scheme on the desired terminated peptide sequence.

In certain cases, the peptide sequence may be constructed by reaction of a free acid function of an N-protected amino acid or peptide with the free amine function of a C-protected amino acid or peptide. For example, the hexapeptides may be constructed by coupling the free amine function of a C-protected dipeptide with the free acid function of an N-protected tetrapeptide. This N-protected tetrapeptide may itself be obtained by coupling the free amine function of a C-protected dipeptide with the free acid function of an N-protected dipeptide followed by deprotection of the C-terminal end.

In one preferred embodiment, the amino acids used according to the invention are synthetic peptides.

Preferably, the protecting groups are chosen so as to be removed, respectively, under separate operating conditions.

The amino acids used according to the invention may also be produced by microorganisms, using bioengineering methods. In this case, it may be necessary to extract and purify the peptide from the producing microorganisms, before formulation. Alternatively, the producing microorganism may be applied directly onto the site to be treated on the user.

The compounds of formula (I) in accordance with the invention are preferably used in amounts ranging from 0.001% to 20% of the total weight of the composition, more preferentially in an amount representing from 0.01% to 10% of the total weight of the composition, or, even more preferentially, 0.1% to 5%. The amounts of active agent will be adapted as a function of the galenical form of the composition containing them.

The compounds of formula (I) and the salts thereof, the optical isomers, stereoisomers, enantiomers and diastereoisomers thereof or the geometrical isomers thereof are novel, with the exception of the following compounds (a) and (b):

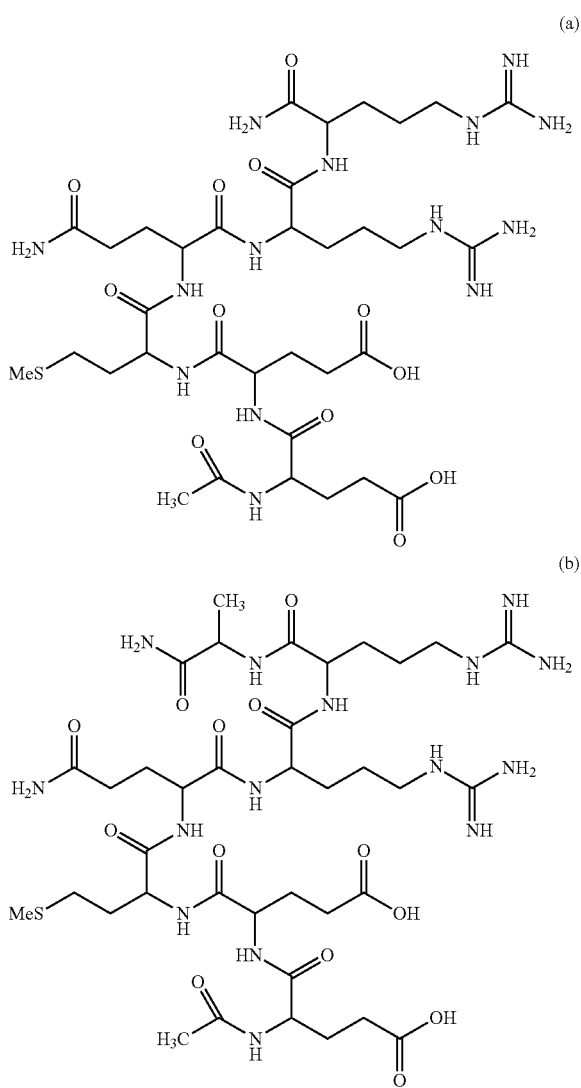

(a)

(b)

They constitute another subject of the invention.

Another subject of the invention consists of a cosmetic composition comprising, in a cosmetically acceptable medium, at least one compound of formula (I) as defined previously, with the exception of compounds (a) and (b) below:

Galenical Forms

The composition according to the invention may be in any galenical form conventionally used for topical application and especially in the form of aqueous gels, or aqueous or aqueous-alcoholic solutions. By adding a fatty or oily phase, it may also be in the form of dispersions of lotion type, emulsions of liquid or semi-liquid consistency of the milk type, obtained by dispersing a fatty phase in an aqueous phase (O/W) or conversely (W/O), or suspensions or emulsions of soft, semi-solid or solid consistency of the cream or gel type, or alternatively multiple emulsions (W/O/W or O/W/O), microemulsions, vesicular dispersions of ionic and/or nonionic type, or wax/aqueous phase dispersions. These compositions are prepared according to the usual methods.

The invention also relates to compositions conditioned in pressurized form in an aerosol device or in a pump-dispenser bottle; conditioned in a device equipped with a perforated wall, especially a grille; conditioned in a device equipped with a ball applicator ("roll-on"); characterized in that they contain at least perlite particles as defined previously. In this regard, they contain the ingredients generally used in products of this type, which are well known to those skilled in the art.

According to one particular form of the invention, the compositions according to the invention may be anhydrous.

The term "anhydrous composition" means a composition containing less than 2% by weight of water, or even less than 0.5% water, and especially free of water, the water not being added during the preparation of the composition but corresponding to the residual water provided by the mixed ingredients.

The antiperspirant compositions according to the invention may also be in the form of sticks.

According to one particular form of the invention, the compositions for treating perspiration according to the invention may also be in the form of loose or compacted powder.

The compositions according to the invention intended for cosmetic use may comprise at least one aqueous phase. They are especially formulated as aqueous lotions or as water-in-oil or oil-in-water emulsions or as multiple emulsions (oil-in-water-in-oil or water-in-oil-in-water triple emulsion (such emulsions are known and described, for example, by C. Fox in "Cosmetics and Toiletries"—November 1986—Vol. 101—pages 101-112)).

Aqueous Phase

The aqueous phase of the said compositions contains water and generally other water-soluble or water-miscible solvents. The water-soluble or water-miscible solvents comprise monoalcohols with a short chain, for example of $C_1$-$C_4$, such as ethanol or isopropanol; diols or polyols, for instance ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. Propylene glycol and glycerol, propane-1,3-diol, will be used more particularly.

Emulsifiers a) Oil-in-Water Emulsifiers

As emulsifiers that may be used in the oil-in-water emulsions or oil-in-water-in-oil triple emulsions, examples that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof, such as the mixture of glyceryl stearate and PEG-40 stearate.

Mention may also be made of fatty alcohol/alkylpolyglycoside emulsifying mixtures as described in patent applications WO 92/06778, WO 95/13863 and WO 98/47610, for instance the commercial products sold by the company SEPPIC under the name Montanov®.

b) Water-in-Oil Emulsifiers

Among the emulsifiers that may be used in the water-in-oil emulsions or water-in-oil-in-water-in-oil triple emulsions, examples that may be mentioned include alkyl dimethicone copolyols corresponding to formula (I) below

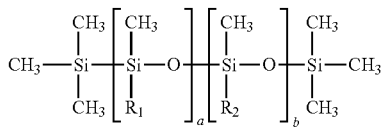

(I)

in which:

R₁ denotes a linear or branched $C_{12}$-$C_{20}$ and preferably $C_{12}$-$C_{18}$ alkyl group;

R₂ denotes the group: —$C_nH_{2n}$—(—$OC_2H_4$—)$_x$—(—$OC_3H_6$—)$_y$—O—R₃,

R₃ denotes a hydrogen atom or a linear or branched alkyl radical comprising from 1 to 12 carbon atoms;

a is an integer ranging from 1 to 500;

b is an integer ranging from 1 to 500;

n is an integer ranging from 2 to 12 and preferably from 2 to 5;

x is an integer ranging from 1 to about 50 and preferably from 1 to 30;

y is an integer ranging from 0 to about 49 and preferably from 0 to 29, with the proviso that when y is other than zero, the ratio x/y is greater than 1 and preferably ranges from 2 to 11.

Among the alkyl dimethicone copolyol emulsifiers of formula (I) that are preferred, mention will be made more particularly of Cetyl PEG/PPG-10/1 Dimethicone and more particularly the mixture Cetyl PEG/PPG-10/1 Dimethicone and Dimethicone (INCI name), for instance the product sold under the trade name Abil EM90 by the company Goldschmidt, or alternatively the mixture (Polyglyceryl-4 Stearate and Cetyl PEG/PPG-10 (and) Dimethicone (and) Hexyl Laurate), for instance the product sold under the trade name Abil WE09 by the same company.

Among the water-in-oil emulsifiers, mention may also be made of the dimethicone copolyols corresponding to formula (II) below

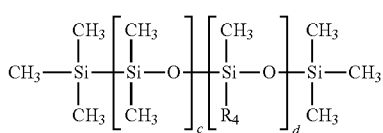

(II)

in which

R₄ denotes the group: —$C_mH_{2m}$—(—$OC_2H_4$—)$_s$—(—$OC_3H_6$—)$_t$—O—R₅,

R₅ denotes a hydrogen atom or a linear or branched alkyl radical comprising from 1 to 12 carbon atoms, c is an integer ranging from 1 to about 500;

d is an integer ranging from 1 to about 500;

m is an integer ranging from 2 to 12 and preferably from 2 to 5;

s is an integer ranging from 1 to about 50 and preferably from 1 to 30;

t is an integer ranging from 0 to about 50 and preferably from 0 to 30; with the proviso that the sum s+t is greater than or equal to 1.

Among these preferential dimethicone copolyol emulsifiers of formula (II), use will particularly be made of PEG-18/PPG-18 Dimethicone and more particularly the mixture Cyclopentasiloxane (and) PEG-18/PPG-18 Dimethicone (INCI name), such as the product sold by the company Dow Corning under the trade name Silicone DC5225 C or KF-6040 from the company Shin-Etsu.

According to one particularly preferred form, use will be made of a mixture of at least one emulsifier of formula (I) and of at least one emulsifier of formula (II).

Use will be made more particularly of a mixture of PEG-18/PPG-18 Dimethicone and Cetyl PEG/PPG-10/1 Dimethicone and even more particularly a mixture of (Cyclopentasiloxane (and) PEG-18/PPG-18 Dimethicone) and of Cetyl PEG/PPG-10/1 Dimethicone and Dimethicone or of (Polyglyceryl-4-stearate and Cetyl PEG/PPG-10 (and) Dimethicone (and) Hexyl Laurate).

Among the water-in-oil emulsifiers, mention may also be made of nonionic emulsifiers derived from fatty acids and polyol, alkylpolyglycosides (APG) and sugar esters, and mixtures thereof.

As nonionic emulsifiers derived from fatty acids and polyol, use may be made especially of fatty acid esters of polyol, the fatty acid especially containing a C8-C24 alkyl chain, and the polyols being, for example, glycerol and sorbitan.

Fatty acid esters of polyol that may especially be mentioned include isostearic acid esters of polyols, stearic acid esters of polyols, and mixtures thereof, in particular isostearic acid esters of glycerol and/or sorbitan.

Stearic acid esters of polyols that may especially be mentioned include the polyethylene glycol esters, for instance PEG-30 Dipolyhydroxystearate, such as the product sold under the name Arlacel P135 by the company ICI.

Glycerol and/or sorbitan esters that may be mentioned, for example, include polyglyceryl isostearate, such as the product sold under the name Isolan GI 34 by the company Goldschmidt; sorbitan isostearate, such as the product sold under the name Arlacel 987 by the company ICI; sorbitan glyceryl isostearate, such as the product sold under the name Arlacel 986 by the company ICI, the mixture of sorbitan isostearate and polyglyceryl isostearate (3 mmol) sold under the name Arlacel 1690 by the company Uniqema, and mixtures thereof.

The emulsifier may also be chosen from alkylpolyglycosides with an HLB of less than 7, for example those represented by the general formula (1) below:

R—O-(G)x    (1)

in which R represents a branched and/or unsaturated alkyl radical comprising from 14 to 24 carbon atoms, G represents a reduced sugar comprising 5 or 6 carbon atoms, and x is a value ranging from 1 to 10 and preferably from 1 to 4, and G especially denotes glucose, fructose or galactose.

The unsaturated alkyl radical may comprise one or more ethylenic unsaturations, and in particular one or two ethylenic unsaturations.

As alkylpolyglycosides of this type, mention may be made of alkylpolyglucosides (G=glucose in formula (I)), and especially the compounds of formula (I) in which R more particularly represents an olelyl radical (unsaturated C18 radical) or isostearyl (saturated C18 radical), G denotes glucose, x is a value ranging from 1 to 2, especially isostearyl-glucoside or oleyl-glucoside, and mixtures thereof. This alkylpolyglucoside may be used as a mixture with a coemulsifier, more especially with a fatty alcohol and especially a fatty alcohol containing the same fatty chain as that of the alkylpolyglucoside, i.e. comprising from 14 to 24 carbon atoms and containing a branched and/or unsaturated chain, for example isostearyl alcohol when the alkylpolyglucoside is isostearyl glucoside, and oleyl alcohol when the alkylpolyglucoside is oleyl glucoside, optionally in the form of a self-emulsifying composition, as described, for example, in document WO-A-

92/06778. Use may be made, for example, of the mixture of isostearyl glucoside and isostearyl alcohol, sold under the name Montanov WO 18 by the company SEPPIC, and also the mixture octyldodecanol and octyldodecyl xyloside sold under the name Fludanov 20× by the company SEPPIC.

Mention may also be made of succinic-terminated polyolefins, for instance esterified succinic-terminated polyisobutylenes and salts thereof, especially the diethanolamine salts, such as the commercial products sold under the names Lubrizol 2724, Lubrizol 2722 and Lubrizol 5603 by the company Lubrizol or the commercial product Chemcinnate 2000.

The total amount of emulsifiers in the composition will preferably be, in the composition according to the invention, in active material contents ranging from 1% to 8% by weight and more particularly from 2% to 6% by weight relative to the total weight of the composition.

Fatty Phase

The compositions according to the invention may contain at least one water-immiscible organic liquid phase. This phase generally comprises one or more hydrophobic compounds that make the said phase water immiscible. The said phase is liquid (in the absence of structuring agent) at room temperature (20-25° C.). Preferentially, the water-immiscible organic-liquid organic phase in accordance with the invention generally comprises at least one volatile oil and/or non-volatile oil and optionally at least one structuring agent.

The term "oil" means a fatty substance that is liquid at room temperature (25° C.) and atmospheric pressure (760 mmHg, i.e. $10^6$ Pa). The oil may be volatile or non-volatile.

For the purposes of the invention, the term "volatile oil" means an oil that is capable of evaporating on contact with the skin or the keratin fibre in less than one hour, at room temperature and atmospheric pressure. The volatile oils of the invention are volatile cosmetic oils, which are liquid at room temperature, having a non-zero vapour pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" means an oil that remains on the skin or the keratin fibre at room temperature and atmospheric pressure for at least several hours, and that especially has a vapour pressure of less than $10^{-3}$ mmHg (0.13 Pa).

The oil may be chosen from any physiologically acceptable oil and in particular cosmetically acceptable oil, especially mineral, animal, plant or synthetic oils; in particular volatile or nonvolatile hydrocarbon-based oils and/or silicone oils and/or fluoro oils, and mixtures thereof.

More precisely, the term "hydrocarbon-based oil" means an oil mainly comprising carbon and hydrogen atoms and optionally one or more functions chosen from hydroxyl, ester, ether and carboxylic functions. Generally, the oil has a viscosity of from 0.5 to 100 000 mPa·s, preferably from 50 to 50 000 mPa·s and more preferably from 100 to 300 000 mPa·s.

As examples of volatile oils that may be used in the invention, mention may be made of:
volatile hydrocarbon-based oils chosen from hydrocarbon-based oils containing from 8 to 16 carbon atoms, and especially $C_8$-$C_{16}$ isoalkanes of petroleum origin (also known as isoparaffins), for instance isododecane (also known as 2,2,4,4,6-pentamethylheptane), isodecane and isohexadecane, for example the oils sold under the trade names Isopar or Permethyl, branched $C_8$-$C_{16}$ esters and isohexyl neopentanoate, and mixtures thereof. Other volatile hydrocarbon-based oils, for instance petroleum distillates, especially those sold under the name Shell Solt by the company Shell, may also be used; volatile linear alkanes, such as those described in patent application WO 2007/068 371.

volatile silicones, for instance volatile linear or cyclic silicone oils, especially those with a viscosity ≤8 centistokes ($8 \times 10^{-6}$ m²/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane; and mixtures thereof.

Mention may also be made of linear volatile alkyltrisiloxane oils of general formula (I):

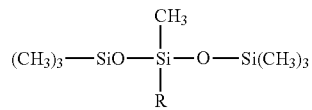

in which R represents an alkyl group containing from 2 to 4 carbon atoms, of which one or more hydrogen atoms may be substituted with a fluorine or chlorine atom.

Among the oils of general formula (I) that may be mentioned are:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is, respectively, a butyl group, a propyl group or an ethyl group.

As examples of nonvolatile oils that may be used in the invention, mention may be made of:
hydrocarbon-based oils of animal origin, such as perhydrosqualene;
hydrocarbon-based plant oils such as liquid triglycerides of fatty acids of 4 to 24 carbon atoms, for instance heptanoic or octanoic acid triglycerides, or wheatgerm oil, olive oil, sweet almond oil, palm oil, rapeseed oil, cottonseed oil, alfalfa oil, poppy oil, pumpkin oil, marrow oil, blackcurrant oil, evening primrose oil, millet oil, barley oil, quinoa oil, rye oil, safflower oil, candlenut oil, passion flower oil, musk rose oil, sunflower oil, corn oil, soybean oil, grapeseed oil, sesame seed oil, hazelnut oil, apricot oil, macadamia oil, castor oil, avocado oil, caprylic/capric acid triglycerides, for instance those sold by the company Stéarineries Dubois or those sold under the names Miglyol 810, 812 and 818 by the company Dynamit Nobel, jojoba oil and shea butter oil,
linear or branched hydrocarbons, of mineral or synthetic origin, such as liquid paraffins and derivatives thereof, petroleum jelly, polydecenes, polybutenes, hydrogenated polyisobutene such as Parleam, and squalane,
synthetic ethers containing from 10 to 40 carbon atoms;
synthetic esters, especially of fatty acids, for instance the oils of formula $R_1COOR_2$ in which $R_1$ represents a linear or branched higher fatty acid residue containing from 1 to 40 carbon atoms and $R_2$ represents a hydrocarbon-based chain, which is especially branched, containing from 1 to 40 carbon atoms, with $R_1 + R_2 \geq 10$, for instance purcellin oil (cetostearyl octanoate), isononyl isononanoate, isopropyl myristate, isopropyl palmitate, $C_{12}$-$C_{15}$ alkyl benzoates, hexyl laurate, diisopropyl adipate, isononyl isononanoate, 2-ethylhexyl palmitate, 2-octyldodecyl stearate, 2-octyldodecyl erucate, isostearyl isostearate or tridecyl trimellitate; alcohol or polyalcohol octanoates, decanoates or ricinoleates, for instance propylene glycol dioctanoate; hydroxylated esters, for instance isostearyl lactate, octyl hydroxystearate, octyldodecyl hydroxystearate, diisostearyl malate, triisocetyl citrate, and fatty alcohol heptanoates, octanoates or decanoates; polyol esters, for instance propylene glycol dioctanoate, neopentyl glycol diheptanoate or diethylene glycol diisononanoate; and pentaerythritol esters, for instance pentaerythrityl tetraisostearate, fatty alcohols that are liquid at room temperature, containing a branched and/or unsaturated carbon-based chain containing from 12 to 26 carbon atoms, for instance octyldodecanol, isostearyl alcohol, 2-butyloctanol, 2-hexyldecanol, 2-undecylpentadecanol or oleyl alcohol, higher fatty acids such as oleic acid, linoleic acid or linolenic acid, carbonates;

acetates;

citrates;

fluoro oils that are optionally partially hydrocarbon-based and/or silicone-based, for instance fluorosilicone oils, fluoro polyethers and fluorosilicones as described in document EP-A-847 752;

silicone oils, for instance linear or cyclic non-volatile polydimethylsiloxanes (PDMS); polydimethylsiloxanes comprising alkyl, alkoxy or phenyl groups, which are pendant or at the end of a silicone chain, these groups containing from 2 to 24 carbon atoms; phenyl silicones, for instance phenyl trimethicones, phenyl dimethicones, phenyl trimethylsiloxy diphenyl siloxanes, diphenyl dimethicones, diphenyl methyldiphenyl trisiloxanes and 2-phenylethyl trimethylsiloxy silicates, and mixtures thereof.

Structuring Agent

The compositions according to the invention comprising a fatty phase may also contain at least one agent for structuring the said fatty phase, which may preferably be chosen from waxes, pasty compounds, and mineral or organic lipophilic gelling agents, and mixtures thereof.

It is understood that the amount of these compounds may be adjusted by a person skilled in the art so as not to harm the desired effect in the context of the present invention.

Wax(es)

The wax is in general a lipophilic compound that is solid at room temperature (25° C.), with a solid/liquid reversible change of state, having a melting point of greater than or equal to 30° C., which may be up to 200° C. and in particular up to 120° C.

In particular, the waxes that are suitable for the invention may have a melting point of greater than or equal to 45° C. and in particular greater than or equal to 55° C.

For the purposes of the invention, the melting point corresponds to the temperature of the most endothermic peak observed on thermal analysis (DSC) as described in standard ISO 11357-3; 1999. The melting point of the wax may be measured using a differential scanning calorimeter (DSC), for example the calorimeter sold under the name MDSC 2920 by the company TA Instruments.

The Measuring Protocol is as Follows:

A sample of 5 mg of wax placed in a crucible is subjected to a first temperature rise ranging from −20° C. to 100° C., at a heating rate of 10° C./minute, it is then cooled from 100° C. to −20° C. at a cooling rate of 10° C./minute and is finally subjected to a second temperature increase ranging from −20° C. to 100° C. at a heating rate of 5° C./minute. During the second temperature increase, the variation of the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The waxes that may be used in the compositions according to the invention are chosen from waxes that are solid at room temperature of animal, plant, mineral or synthetic origin, and mixtures thereof.

As illustrations of waxes that are suitable for the invention, mention may be made especially of hydrocarbon-based waxes, for instance beeswax, lanolin wax, Chinese insect waxes, rice bran wax, carnauba wax, candelilla wax, ouricury wax, esparto grass wax, berry wax, shellac wax, Japan wax and sumach wax; montan wax, orange wax and lemon wax, refined sunflower wax sold under the name Sunflower Wax by Koster Keunen, microcrystalline waxes, paraffins and ozokerite; polyethylene waxes, the waxes obtained by Fischer-Tropsch synthesis and waxy copolymers, and also esters thereof.

Mention may also be made of waxes obtained by catalytic hydrogenation of animal or plant oils containing linear or branched $C_8$-$C_{32}$ fatty chains. Among these waxes that may especially be mentioned are isomerized jojoba oil such as the trans-isomerized partially hydrogenated jojoba oil manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylolpropane) tetrastearate sold under the name Hest 2T-4S® by the company Heterene.

Mention may also be made of silicone waxes ($C_{30-45}$ alkyl dimethicone) and fluoro waxes.

The waxes obtained by hydrogenation of castor oil esterified with cetyl alcohol, sold under the names Phytowax ricin 16L64® and 22L73® by the company Sophim, may also be used. Such waxes are described in patent application FR-A-2 792 190.

A wax that may be used is a $C_{20}$-$C_{40}$ alkyl (hydroxystearyloxy)stearate (the alkyl group containing from 20 to 40 carbon atoms), alone or as a mixture.

Such a wax is especially sold under the names Kester Wax K 82 P®, Hydroxypolyester K 82 P® and Kester Wax K 80 P® by the company Koster Keunen.

As microwaxes that may be used in the compositions according to the invention, mention may be made especially of carnauba microwaxes, such as the product sold under the name MicroCare 350® by the company Micro Powders, synthetic microwaxes, such as the product sold under the name MicroEase 1145® by the company Micro Powders, microwaxes consisting of a mixture of carnauba wax and polyethylene wax, such as the products sold under the names Micro Care 300® and 310® by the company Micro Powders, microwaxes consisting of a mixture of carnauba wax and of synthetic wax, such as the product sold under the name Micro Care 325® by the company Micro Powders, polyethylene microwaxes, such so as the products sold under the names Micropoly 200®, 220®, 220L® and 250S® by the company Micro Powders, the commercial products Performalene 400, Polyethylene and Performalene 500-L Polyethylene from New Phase Technologies, Performalene 655, Polyethylene or paraffin waxes, for instance the wax having the INCI name Microcrystalline Wax and Synthetic Wax and sold under the trade name Microlease by the company Sochibo; polytetrafluoroethylene microwaxes such as those sold under the names Microslip 519® and 519 L® by the company Micro Powders.

The composition according to the invention may preferably comprise a content of wax(es) ranging from 3% to 20% by weight relative to the total weight of the composition, in particular from 5% to 15% and more particularly from 6% to 15% thereof.

Pasty Compounds

For the purposes of the present invention, the term "pasty compound" is intended to denote a lipophilic fatty compound that undergoes a reversible solid/liquid change of state and that comprises, at a temperature of 23° C., a liquid fraction and a solid fraction.

The pasty compound is preferably chosen from synthetic compounds and compounds of plant origin. A pasty compound may be obtained by the synthesis from starting materials of plant origin.

The pasty compound may be advantageously chosen from:
lanolin and derivatives thereof,
polymeric or non-polymeric silicone compounds,
polymeric or non-polymeric fluoro compounds,
vinyl polymers, especially:
olefin homopolymers,
olefin copolymers,
hydrogenated diene homopolymers and copolymers,
linear or branched oligomers, homopolymers or copolymers of alkyl (meth)acrylates preferably containing a C8-C30 alkyl group,
oligomers, which are homopolymers and copolymers of vinyl esters containing C8-C30 alkyl groups, and
oligomers, which are homopolymers and copolymers of vinyl esters containing C8-C30 alkyl groups,
liposoluble polyethers resulting from the polyetherification between one or more C2-C100 and preferably C2-C50 diols,
esters,
mixtures thereof.

Among the esters, the following are especially preferred:
esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, especially such as those sold under the brand name Softisan 649 by the company Sasol,
the arachidyl propionate sold under the brand name Waxenol 801 by Alzo,
phytosterol esters,
fatty acid triglycerides and derivatives thereof,
pentaerythritol esters,
non-crosslinked polyesters resulting from polycondensation between a linear or branched C4-C50 dicarboxylic acid or polycarboxylic acid and a C2-C50 diol or polyol,
aliphatic esters of an ester, resulting from the esterification of an aliphatic hydroxycarboxylic acid ester with an aliphatic carboxylic acid,
polyesters resulting from the esterification, with a polycarboxylic acid, of an aliphatic hydroxycarboxylic acid ester, the said ester comprising at least two hydroxyl groups, such as the products Risocast DA-H® and Risocast DA-L®,
esters of a diol dimer and of a diacid dimer, where appropriate esterified on their free alcohol or acid function(s) with acid or alcohol radicals, such as Plandool-G,
mixtures thereof.

Among the pasty compounds of plant origin that will preferably be chosen is a mixture of oxyethylenated (5 OE) oxypropylenated (5 OP) soybean sterols and pentaerythritol, sold under the reference Lanolide by the company Vevy.

Lipophilic Gelling Agents

Mineral Gelling Agents

Mineral lipophilic gelling agents that may be mentioned include optionally modified clays, for instance hectorites modified with a C10-C22 ammonium chloride, for instance hectorite modified with distearyldimethylammonium chloride, for instance the product sold under the name Bentone 38V® by the company Elementis.

Mention may also be made of fumed silica optionally subjected to a hydrophobic surface treatment, the particle size of which is less than 1 μm. Specifically, it is possible to chemically modify the surface of the silica, by chemical reaction generating a reduced number of silanol groups present at the surface of the silica. It is especially possible to substitute silanol groups with hydrophobic groups: a hydrophobic silica is then obtained. The hydrophobic groups may be trimethylsiloxyl groups, which are obtained especially by treating fumed silica in the presence of hexamethyldisilazane. Silicas thus treated are known as "silica silylate" according to the CTFA (8th Edition, 2000). They are sold, for example, under the references Aerosil R812® by the company Degussa, Cab-O-Sil TS-530® by the company Cabot, dimethylsilyloxyl or polydimethylsiloxane groups, which are obtained especially by treating fumed silica in the presence of polydimethylsiloxane or dimethyldichlorosilane. Silicas thus treated are known as "silica dimethyl silylate" according to the CTFA (8th Edition, 2000). They are sold, for example, under the references Aerosil R972® and Aerosil R974® by the company Degussa, and Cab-O-Sil TS-610® and Cab-O-Sil TS-720® by the company Cabot.

The hydrophobic fumed silica preferably has a particle size that may be nanometric to micrometric, for example ranging from about 5 to 200 nm.

Organic Gelling Agents

The polymeric organic lipophilic gelling agents are, for example, partially or totally crosslinked elastomeric organopolysiloxanes of three-dimensional structure, for instance those sold under the names KSG6®, KSG16® and KSG18® from Shin-Etsu, Trefil E-505C® or Trefil E-506C® from Dow Corning, Gransil SR-CYC®, SR DMF10®, SR-DC556®, SR 5CYC Gel®, SR DMF 10 Gel® and SR DC 556 Gel® from Grant Industries and SF 1204® and JK 113® from General Electric; ethylcellulose, for instance the product sold under the name Ethocel® by Dow Chemical; galactomannans comprising from one to six and in particular from two to four hydroxyl groups per saccharide, substituted with a saturated or unsaturated alkyl chain, for instance guar gum alkylated with C1 to C6, and in particular C1 to C3, alkyl chains, and mixtures thereof. Block copolymers of "diblock", "triblock" or "radial" type, of the polystyrene/polyisoprene or polystyrene/polybutadiene type, such as the products sold under the name Luvitol HSB® by the company BASF, of the polystyrene/copoly(ethylene-propylene) type, such as the products sold under the name Kraton® by the company Shell Chemical Co., or of the polystyrene/copoly(ethylene-butylene) type, and mixtures of triblock and radial (star) copolymers in isododecane, such as those sold by the company Penreco under the name Versagel®, for instance the mixture of butylene/ethylene/styrene triblock copolymer and of ethylene/propylene/styrene star copolymer in isododecane (Versagel M 5960).

Lipophilic gelling agents that may also be mentioned include polymers with a weight-average molecular mass of less than 100 000, comprising a) a polymer backbone with hydrocarbon-based repeating units containing at least one heteroatom, and optionally b) at least one optionally functionalized pendent fatty chain and/or terminal fatty chain, containing from 6 to 120 carbon atoms and being linked to these hydrocarbon-based units, as described in patent applications WO-A-02/056 847 and WO-A-02/47619, the content of which is incorporated by reference; in particular, polyamide resins (especially comprising alkyl groups containing from 12 to 22 carbon atoms) such as those described in U.S. Pat. No. 5,783,657, the content of which is incorporated by reference.

Among the lipophilic gelling agents that may be used in the compositions according to the invention, mention may also be made of fatty acid esters of dextrin, such as dextrin palmitates, especially the products sold under the name Rheopearl TL® or Rheopearl KL® by the company Chiba Flour.

Silicone polyamides of the polyorganosiloxane type may also be used, such as those described in documents U.S. Pat. Nos. 5,874,069, 5,919,441, 6,051,216 and 5,981,680.

These silicone polymers may belong to the following two families:
- polyorganosiloxanes comprising at least two groups capable of establishing hydrogen interactions, these two groups being in the chain of the polymer, and/or
- polyorganosiloxanes comprising at least two groups capable of establishing hydrogen interactions, these two groups being located on grafts or branches.

Aluminium and/or Zirconium Salts or Complexes

The compositions according to the invention may also contain one or more aluminium and/or zirconium salts or complexes.

The antiperspirant salts or complexes in accordance with the invention are generally chosen from aluminium and/or zirconium salts or complexes. They are preferably chosen from aluminium halohydrates; aluminium zirconium halohydrates, complexes of zirconium hydroxychloride and of aluminium hydroxychloride with or without an amino acid, such as those described in U.S. Pat. No. 3,792,068.

Among the aluminium salts, mention may be made in particular of aluminium chlorohydrate in activated or unactivated form, aluminium chlorohydrex, the aluminium chlorohydrex-polyethylene glycol complex, the aluminium chlorohydrex-propylene glycol complex, aluminium dichlorohydrate, the aluminium dichlorohydrex-polyethylene glycol complex, the aluminium dichlorohydrex-propylene glycol complex, aluminium sesquichlorohydrate, the aluminium sesquichlorohydrex-polyethylene glycol complex, the aluminium sesquichlorohydrex-propylene glycol complex, aluminium sulfate buffered with sodium aluminium lactate.

Among the aluminium-zirconium salts, mention may be made in particular of aluminium zirconium octachlorohydrate, aluminium zirconium pentachlorohydrate, aluminium zirconium tetrachlorohydrate and aluminium zirconium trichlorohydrate.

The complexes of zirconium hydroxychloride and of aluminium hydroxychloride with an amino acid are generally known as ZAG (when the amino acid is glycine). Among these products, mention may be made of the complexes aluminium zirconium octachlorohydrex glycine, aluminium zirconium pentachlorohydrex glycine, aluminium zirconium tetrachlorohydrex glycine and aluminium zirconium trichlorohydrex glycine.

The antiperspirant salts or complexes may be present in the composition according to the invention in a proportion from about 0.5% to 25% by weight relative to the total weight of the composition.

Deodorant Active Agents

The compositions according to the invention may also contain one or more deodorant active agents.

The deodorant active agents may be bacteriostatic agents or bactericides that act on underarm odour microorganisms, such as 2,4,4'-trichloro-2'-hydroxydiphenyl ether (®Triclosan), 2,4-dichloro-2'-hydroxydiphenyl ether, 3',4',5'-trichlorosalicylanilide, 1-(3',4'-dichlorophenyl)-3-(4'-chlorophenyl)urea (®Triclocarban) or 3,7,11-trimethyldodeca-2,5,10-trienol (®Farnesol); quaternary ammonium salts such as cetyltrimethylammonium salts, cetylpyridinium salts, DPTA (1,3-diaminopropanetetraacetic acid), 1,2-decanediol (Symclariol from the so company Symrise), glycerol derivatives, for instance caprylic/capric glycerides (Capmul MCM from Abitec), glyceryl caprylate or caprate (Dermosoft GMCY and Dermosoft GMC, respectively from Straetmans), Polyglyceryl-2 caprate (Dermosoft DGMC from Straetmans), and biguanide derivatives, for instance polyhexamethylene biguanide salts.-chlorhexidine and salts thereof; 4-phenyl-4,4-dimethyl-2-butanol (Symdeo MPP from Symrise).

Among the deodorant active agents in accordance with the invention, mention may also be made of—zinc salts, for instance zinc salicylate, zinc gluconate, zinc pidolate; zinc sulfate, zinc chloride, zinc lactate, zinc phenolsulfonate; zinc ricinoleate;
  sodium bicarbonate;
  salicylic acid and derivatives thereof such as 5-n-octanoyl-salicylic acid;
  silver zeolites or silver-free zeolites;
  alum.

In the event of incompatibility or to stabilize them, some of the active agents mentioned above may be incorporated into spherules, especially ionic or nonionic vesicles and/or nanoparticles (nanocapsules and/or nanospheres).

The deodorant active agents may be present in the composition according to the invention in a proportion from about 0.01% to 5% by weight relative to the total weight of the composition.

Suspension Agents

In order to improve the homogeneity of the product, it is also possible to use one or more suspension agents preferably chosen from hydrophobic modified montmorillonite clays such as hydrophobic modified bentonites or hectorites. Examples that may be mentioned include the product Stearalkonium Bentonite (CTFA name) (product of reaction of bentonite and the quaternary ammonium stearalkonium chloride) such as the commercial product sold under the name Tixogel MP 250 by the company Sud Chemie Rheologicals, United Catalysts Inc. or the product Disteardimonium Hectorite (CTFA name) (product of reaction of hectorite and distearyldimonium chloride) sold under the name Bentone 38 or Bentone Gel by the company Elementis Specialities.

The suspension agents are preferably present in amounts ranging from 0.1% to 5% by weight and more preferentially from 0.2% to 2% by weight relative to the total weight of the composition.

Organic Powder

According to one particular form of the invention, the antiperspirant compositions according to the invention will also contain an organic powder.

In the present patent application, the term "organic powder" means any solid that is insoluble in the medium at room temperature (25° C.).

As organic powders that may be used in the composition of the invention, examples that may be mentioned include polyamide particles and especially those sold under the name Orgasol by the company Atochem; polyethylene powders; microspheres based on acrylic copolymers, such as those made of ethylene glycol dimethacrylate/lauryl methacrylate copolymer, sold by the company Dow Corning under the name Polytrap; polymethyl methacrylate microspheres, sold under the name Microsphere M-100 by the Company Matsumoto or under the name Covabead LH85 by the Company Wackherr; hollow polymethyl methacrylate microspheres (particle size: 6.5-10.5 µm) sold under the name Ganzpearl GMP 0800 by Ganz Chemical; methyl methacrylate/ethylene glycol dimethacrylate copolymer microbeads (size: 6.5-10.5 µm) sold under the name Ganzpearl GMP 0820 by Ganz Chemical or Microsponge 5640 by the company Amcol Health & Beauty Solutions; ethylene-acrylate copolymer powders, such as those sold under the name Flobeads by the company Sumitomo Seika Chemicals; expanded powders such as hollow microspheres and especially microspheres formed from a terpolymer of vinylidene chloride, acrylonitrile and methacrylate and sold under the name Expancel by the company Kemanord Plast under the references 551 DE 12 (particle size of about 12 µm and mass per unit volume of 40 kg/m$^3$), 551 DE 20 (particle size of about 30 µm and mass per unit volume of 65 kg/m$^3$), 551 DE 50 (particle size of about 40 µm), or the microspheres sold under the name Micropearl F 80 ED by the company Matsumoto; powders of natural organic materials such as starch powders, especially of crosslinked or non-crosslinked corn, wheat or rice starch, such as the powders of starch crosslinked with octenylsuccinic anhydride, sold under the name Dry-Flo by the company National Starch; silicone resin microbeads such as those sold under the name Tospearl by the company Toshiba Silicone, especially Tospearl 240; amino acid powders such as the lauroyllysine powder sold under the name Amihope LL-11 by the company Ajinomoto; particles of wax microdispersion, which preferably have mean sizes of less than 1 µm and especially ranging from 0.02 µm to 1 µm, and which are formed essentially from a wax or a mixture of waxes, such as the products sold under the name Aquacer by the company Byk Cera, and especially: Aquacer 520 (mixture of synthetic and natural waxes), Aquacer 514 or 513 (polyethylene wax), Aquacer 511 (polymeric wax), or such as the products sold under the name Jonwax 120 by the company Johnson Polymer (mixture of polyethylene wax and paraffin wax) and under the name Ceraflour 961 by the company Byk Cera (micronized modified polyethylene wax); and mixtures thereof.

Additives

The cosmetic compositions according to the invention may also comprise cosmetic adjuvants chosen from softeners, antioxidants, opacifiers, stabilizers, moisturizers, vitamins, bactericides, preserving agents, polymers, fragrances, thickeners, propellants or any other ingredient usually used in cosmetics for this type of application.

Needless to say, a person skilled in the art will take care to select this or these optional additional compounds such that the advantageous properties intrinsically associated with the cosmetic composition in accordance with the invention are not, or are not substantially, adversely affected by the envisaged addition(s).

The thickeners, which are preferably nonionic, may be chosen from modified or unmodified guar gums and cellulo-ses such as hydroxypropyl guar gum, cetylhydroxyethylcellulose, silicas, for instance Bentone Gel MIO sold by the company NL Industries or Veegum Ultra sold by the company Polyplastic.

The thickeners may also be cationic, for instance Polyquaternium-37 sold under the name Salcare SC95 (Polyquaternium-37 (and) Mineral Oil (and) PPG-1 Trideceth-6) or Salcare SC96 (Polyquaternium-37 (and) Propylene Glycol Dicaprylate/Dicaprate (and) PPG-1 Trideceth-6) or other crosslinked cationic polymers, for instance those of the CTFA name Ethyl Acrylate/Dimethylaminoethyl Methacrylate Cationic Copolymer In Emulsion.

The amounts of these various constituents that may be present in the cosmetic composition according to the invention are those conventionally used in compositions for treating perspiration.

Aerosols

The compositions according to the invention may also be pressurized and may be conditioned in an aerosol device formed by:

(A) a container comprising an antiperspirant composition as defined previously, (B) at least one propellant and a means for dispensing the said aerosol composition.

The propellants generally used in products of this type and that are well known to those skilled in the art are, for instance, dimethyl ether (DME); volatile hydrocarbons such as n-butane, propane, isobutane and mixtures thereof, optionally with at least one chlorohydrocarbon and/or fluorohydrocarbon; among these derivatives, mention may be made of the compounds sold by the company DuPont de Nemours under the names Freon® and Dymel®, and in particular monofluorotrichloromethane, difluorodichloromethane, tetrafluorodichloroethane and 1,1-difluoroethane sold especially under the trade name Dymel 152 A by the company DuPont. Carbon dioxide, nitrous oxide, nitrogen or compressed air may also be used as propellant.

The compositions containing perlite particles as defined previously and the propellant(s) may be in the same compartment or in different compartments in the aerosol container. According to the invention, the concentration of propellant generally ranges from 5% to 95% by weight of pressurized composition, and more preferentially from 50% to 85% by weight relative to the total weight of the pressurized composition.

The dispensing means, which forms a part of the aerosol device, is generally formed by a dispensing valve controlled by a dispensing head, which itself comprises a nozzle via which the aerosol composition is vaporized. The container containing the pressurized composition may be opaque or transparent. It may be made of glass, a polymer or a metal, optionally coated with a protective varnish coat.

The examples that follow serve to illustrate the present invention. The amounts are given as mass percentages relative to the total weight of the composition.

EXAMPLES

Example 1

Anhydrous Stick

POLYETHYLENE WAX
(PERFORMALENE 500-L POLYETHYLENE—NEW PHASE TECHNOLOGIES) 4.1%

ETHYLENE HOMOPOLYMER
(PERFORMALENE 400 POLYETHYLENE—NEW PHASE TECHNOLOGIES) 8.3%
CYCLOHEXADIMETHYLSILOXANE
DOW CORNING 246 FLUID DOW CORNING) 26.4%
PHENYL TRIMETHICONE
(DOW CORNING 556 COSMETIC GRADE FLUID—DOW CORNING) 19.6%
ISOHEXADECANE
19.6%
METHYL METHACRYLATE CROSSPOLYMER
GANZPEARL GMP 0820—GANZ CHEMICAL) 15.0%
COMPOUND 1 6.5%
MICRONIZED ZINC PYRROLIDONECARBOXYLATE
(UCIB—SOLABIA) 0.5%

Procedure:

The cyclopentasiloxane is heated to 65° C. The other ingredients are added (one by one), while remaining at 65-70° C. The whole is homogenized (transparent solution) for 15 minutes. The perlite or the superabsorbent polymer is added. The mixture is cooled to about 55° C. (a few degrees above the thickening point of the mixture)

and is poured into sticks. The sticks are placed at 4° C. for 30 minutes.

Examples 2 and 3

Aerosols

| Ingredients | Ex. 2 | Ex. 3 |
|---|---|---|
| Triethyl citrate | 1.0 | 1.0 |
| (Citroflex 2 (Reilly Chemicals) | | |
| Stearalkonium bentonite Tixogel | 0.2 | 0.2 |
| MP250 (Sud Chemie Rheolog.) | | |
| Isopropyl palmitate | 0.9 | 0.9 |
| COMPOUND 2 | 2.6 | |
| COMPOUND 3 | — | 2.6 |
| Cyclopentasiloxane (and) Dimethiconol | 1.3 | 1.3 |
| (Dow Corning 1501 Fluid) | | |
| (A-31 - Aeropres) | qs 100 | qs 100 |

The invention claimed is:

1. A cosmetic composition comprising as an agent for treating perspiration at least one compound chosen from those corresponding to formula (I) below, or a salt thereof, optical isomers, stereoisomers, enantiomers and diastereoisomers thereof, or a geometrical isomer thereof:

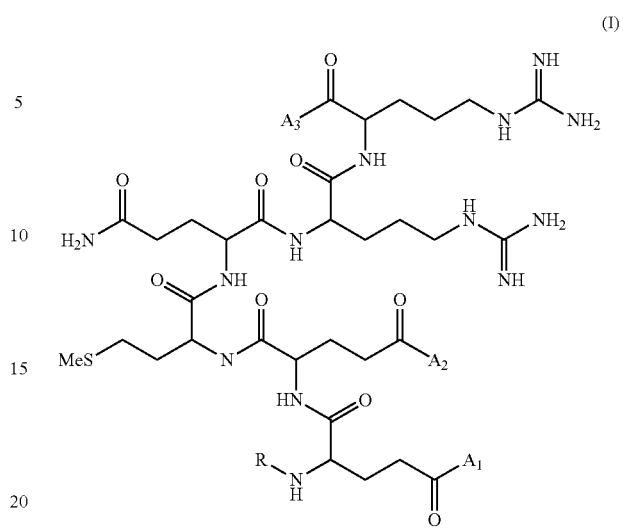

in which:

$A_1$ and $A_2$ independently denote a radical chosen from:

a) —$OR_3$ with $R_3$ denoting a hydrogen atom or a linear or branched, saturated or unsaturated $C_1$-$C_{18}$ alkyl radical;

b) —NH—$(CH_2)_m$—$CO_2H$ with m=0, 1, 2, 3 or 4, c) $NR_1R_2$ with $R_1$ and $R_2$, which may be identical or different, denoting hydrogen or a linear or branched, saturated or unsaturated $C_1$-$C_{12}$ alkyl radical;

d) a group chosen from

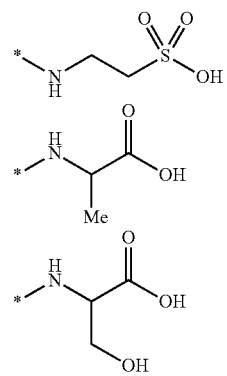

$A_3$ denotes a group chosen from:

(i) $NR_4R_5$ with $R_4$ and $R_5$, which may be identical or different, denoting hydrogen or a linear or branched, saturated or unsaturated $C_1$-$C_{18}$ alkyl radical;

(ii) —$OR'_1$ with $R'_1$ denoting a hydrogen atom or a linear or branched, saturated or unsaturated $C_1$-$C_{18}$ alkyl radical;

(iii) aralkyl;

(iv) —NH—$(CH_2)_m$—$CO_2H$ with m=0, 1, 2, 3 or 4 or alternatively (v) a radical chosen from:

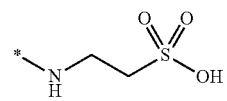

-continued

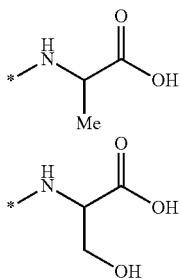

R denotes a radical chosen from:
1) saturated or unsaturated $C_2$-$C_{18}$ acyl;
2) aryl;
3) aralkyl;
4) linear or branched, saturated or unsaturated $C_1$-$C_{12}$ alkyl;
5) a group chosen from the following groups:

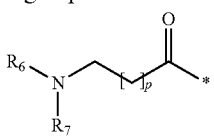

with p = 0, 1, 2, 3

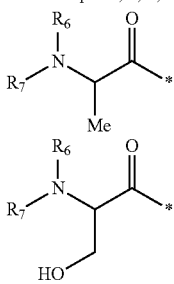

in which $R_6$ and $R_7$, which may be identical or different, denote a hydrogen atom; a linear or branched, saturated or unsaturated $C_1$-$C_{18}$ alkyl radical; a linear or branched, saturated or unsaturated $C_2$-$C_{18}$ acyl radical;
with the exception of compound (a) of structure:

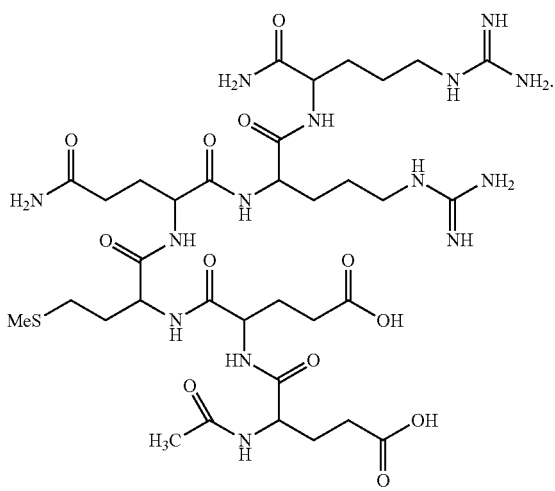

2. The composition according to claim 1, in which the compound of formula (I) or a salt thereof, optical isomers, stereoisomers, enantiomers and diastereoisomers thereof or a geometrical isomer thereof is chosen from those for which:
$A_1$ denotes a radical OH.

3. The composition according to claim 2, in which the compound of formula (I) or a salt thereof, optical isomers, stereoisomers, enantiomers and diastereoisomers thereof or a geometrical isomer thereof is chosen from those for which:
$A_2$ denotes a radical —NH—$(CH_2)_m$—$CO_2$H, and
$A_3$ denotes a radical chosen from:
(i) $NR_4R_5$ or
(ii) —NH—$(CH_2)_m$—$CO_2$H and
R denotes a radical chosen from:
1) saturated or unsaturated $C_2$-$C_6$ acyl
2) linear or branched, saturated or unsaturated $C_1$-$C_{16}$ alkyl
3) a group

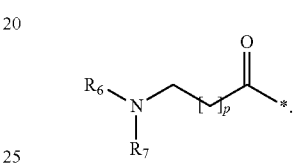

4. A cosmetic process for treating human perspiration and possibly human body odour, which consists in applying to the surface of the skin a composition comprising, in a cosmetically acceptable medium, at least one compound corresponding to formula (I) below, or a salt thereof, optical isomers, stereoisomers, enantiomers and diastereoisomers thereof, or a geometrical isomer thereof:

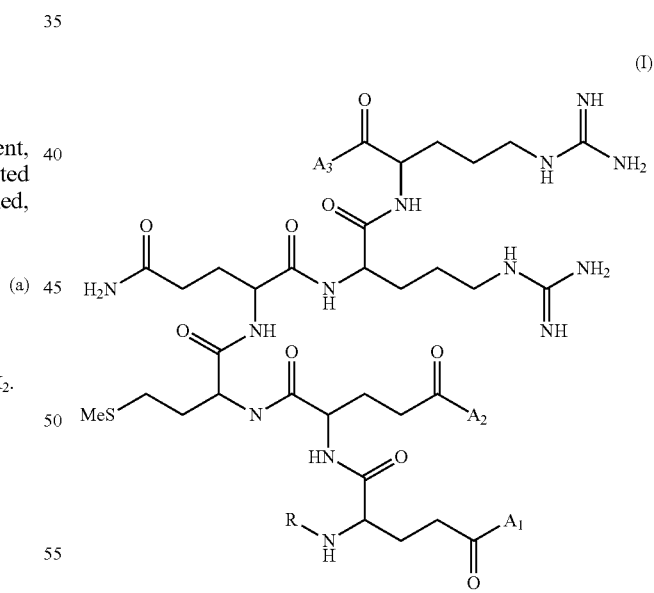

in which:
$A_1$ and $A_2$ independently denote a radical chosen from:
a) —$OR_3$ with $R_3$ denoting a hydrogen atom or a linear or branched, saturated or unsaturated $C_1$-$C_{18}$ alkyl radical;
b) —NH—$(CH_2)_m$—$CO_2$H with m=0, 1, 2, 3 or 4,
c) $NR_1R_2$ with $R_1$ and $R_2$, which may be identical or different, denoting hydrogen or a linear or branched, saturated or unsaturated $C_1$-$C_{12}$ alkyl radical;

d) a group chosen from

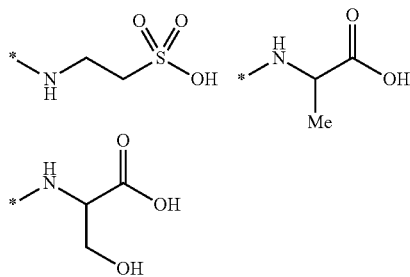

$A_3$ denotes a group chosen from:
(i) $NR_4R_5$ with $R_4$ and $R_5$, which may be identical or different, denoting hydrogen or a linear or branched, saturated or unsaturated $C_1$-$C_{18}$ alkyl radical;
(ii) —$OR'_1$ with $R'_1$ denoting a hydrogen atom or a linear or branched, saturated or unsaturated $C_1$-$C_{18}$ alkyl radical;
(iii) aralkyl;
(iv) —NH—$(CH_2)_m$—$CO_2H$ with m =0, 1, 2, 3 or 4 or alternatively
(v) a radical chosen from:

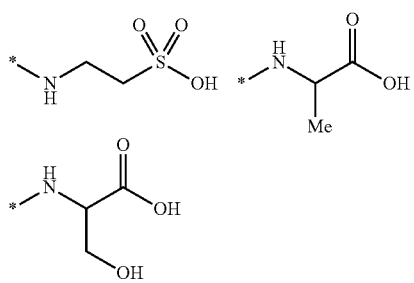

R denotes a radical chosen from:
1) saturated or unsaturated $C_2$-$C_{18}$ acyl;
2) aryl;
3) aralkyl;
4) linear or branched, saturated or unsaturated $C_1$-$C_{12}$ alkyl;
5) a group chosen from the following groups:

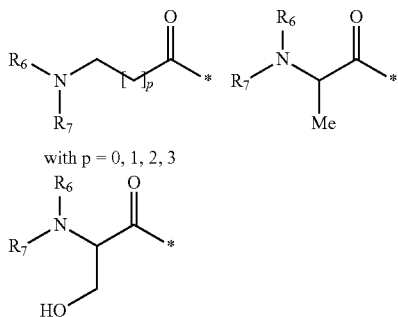

in which $R_6$ and $R_7$, which may be identical or different, denote a hydrogen atom; a linear or branched, saturated or unsaturated $C_1$-$C_{18}$ alkyl radical; a linear or branched, saturated or unsaturated $C_2$-$C_{18}$ acyl radical;

with the exception of compound (a) of structure:

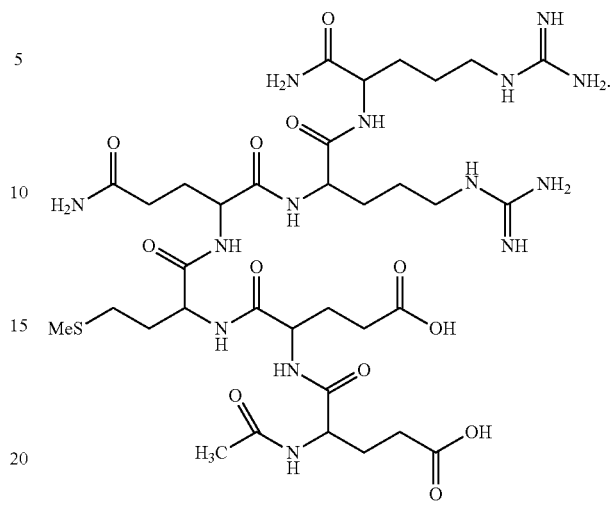

5. A compound corresponding to formula (I) below, or a salt thereof, optical isomers, stereoisomers, enantiomers and diastereoisomers thereof, or a geometrical isomer thereof:

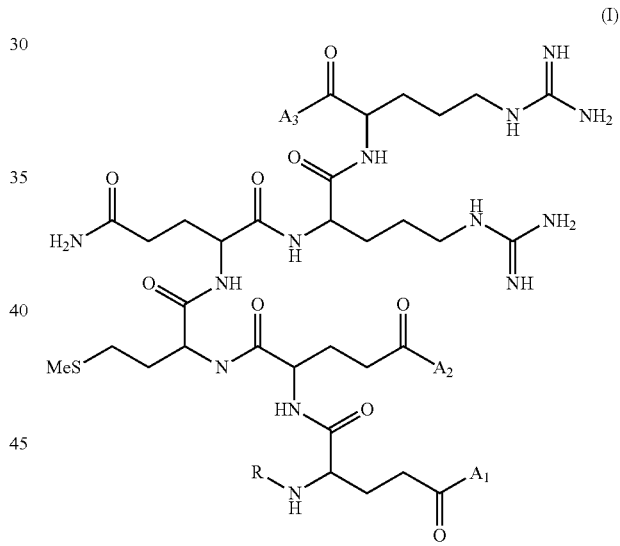

in which:
$A_1$ and $A_2$ independently denote a radical chosen from:
a) —$OR_3$ with $R_3$ denoting a hydrogen atom or a linear or branched, saturated or unsaturated $C_1$-$C_{18}$ alkyl radical;
b) —NH—$(CH_2)_m$—$CO_2H$ with m=0, 1, 2, 3 or 4,
c) $NR_1R_2$ with $R_1$ and $R_2$, which may be identical or different, denoting hydrogen or a linear or branched, saturated or unsaturated $C_1$-$C_{12}$ alkyl radical;
d) a group chosen from

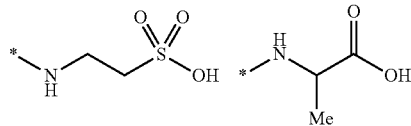

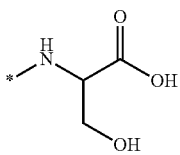

$A_3$ denotes a group chosen from:

(i) $NR_4R_5$ with $R_4$ and $R_5$, which may be identical or different, denoting hydrogen or a linear or branched, saturated or unsaturated $C_1$-$C_{18}$ alkyl radical;

(ii) —$OR'_1$ with $R'_1$ denoting a hydrogen atom or a linear or branched, saturated or unsaturated $C_1$-$C_{18}$ alkyl radical;

(iii) aralkyl;

(iv) —NH—$(CH_2)_m$—$CO_2H$ with m =0, 1, 2, 3 or 4 or alternatively (v) a radical chosen from:

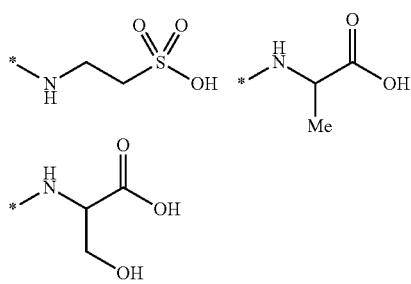

R denotes a radical chosen from:

1) saturated or unsaturated $C_2$-$C_{18}$ acyl;

2) aryl; 3) aralkyl such as benzyl;

4) linear or branched, saturated or unsaturated $C_1$-$C_{12}$ alkyl;

5) a group chosen from the following groups:

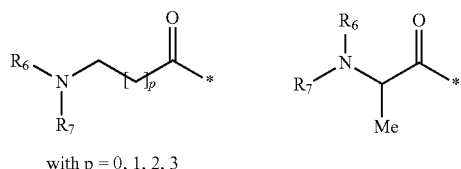

with p = 0, 1, 2, 3

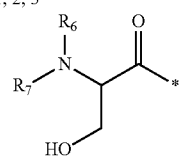

in which $R_6$ and $R_7$, which may be identical or different, denote a hydrogen atom; a linear or branched, saturated or unsaturated $C_1$-$C_{18}$ alkyl radical; a linear or branched, saturated or unsaturated $C_2$-$C_{18}$ acyl radical;

with the exception of compound (a) below:

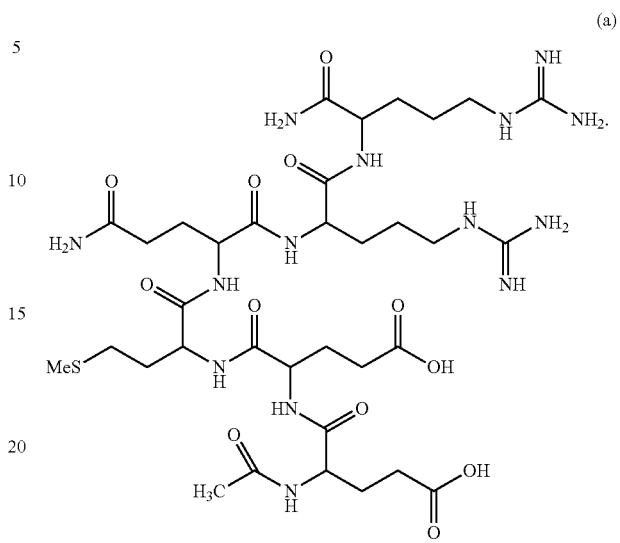

6. A composition comprising, in a cosmetically acceptable medium, at least one compound as defined according to claim 5.

7. The cosmetic process according to claim 4, wherein the compound of formula (I) or a salt thereof, optical isomers, stereoisomers, enantiomers and diastereoisomers thereof or a geometrical isomer thereof is chosen from those for which:

$A_1$ denotes a radical OH.

8. The cosmetic process according to claim 7, wherein the compound of formulat (I) or salt thereof, optical isomers, stereoisomers, enantiomers, and diastereoisomers thereof or a geometrical isomer thereof is chosen from those for which:

$A_2$ denotes a radical —$NH(CH_2)_mCO_2H$, and $A_3$ denotes a radical chosen from:

(i) $NR_4R_5$ or (ii)—NH—$(CH_2)_m$—$CO_2H$ and

R denotes a radical chosen from:

1) saturated or unsaturated $C_2$-$C_6$, acyl 2) liner or branched, saturated or unsaturated $C_1$-$C_{16}$ alkyl 3) a group of structure:

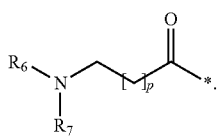

9. The cosmetic process according to claim 8, wherein the compound of formula (I) or a salt thereof, optical isomers, stereoisomers, enantiomers and diastereoisomers thereof or a geometrical isomer thereof is chosen from those for which:

R denotes an acetyl radical, $A_3$ denotes a radical $NH_2$, $A_1$ denotes a hydroxyl radical and $A_2$ denotes a radical —NH—$(CH_2)_m$—$CO_2H$.

10. The cosmetic process according to claim 4, wherein the compound of formula (I) or a salt thereof, optical isomers, stereoisomers, enantiomers and diastereoisomers thereof or a geometrical isomer thereof is chosen from those for which:

$A_1$ denotes a radical —NH13 $(CH_2)_m$—$CO_2H$, or a group chosen from

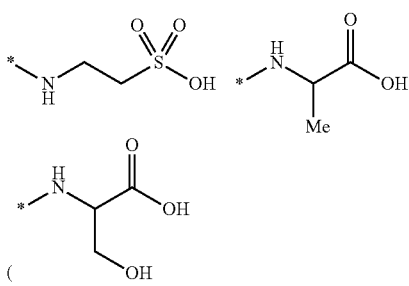

$A_2$ denotes —$OR_3$, a radical —NH—$(CH_2)_m$—$CO_2H$, or a radical chosen from

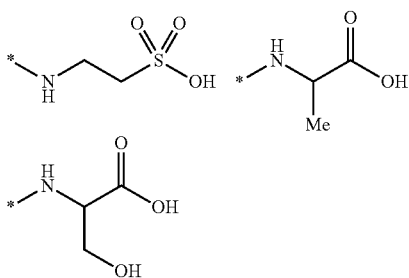

$A_3$ denotes a radical chosen from:
(i) $NR_4R_5$ or
(ii) —NH—$(CH_2)_m$—$CO_2H$
(iii) a radical chosen from

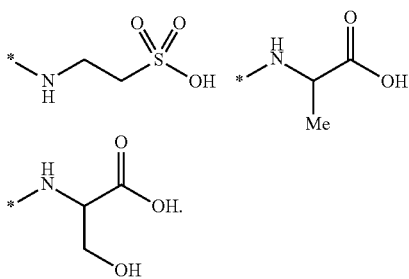

11. The cosmetic process according to claim 9, wherein the compound of formula (I) or salt thereof, optical isomers, stereoisomers, enantiomers and diastereoisomers thereof or a geometrical isomer thereof is chose from those for which:
$A_1$ denotes a radical —$NH(CH_2)_m CO_2H$ and
$A_2$ denotes a radical —$NH(CH_2)_m CO_2H$, or a OH group
$A_3$ denotes a group chosen from:
(i) $NR_4R_5$ with $R_1$ and $R_2$, which may be identical or different, denoting hydrogen or a liner or branched, saturated or unsaturated $C_1$-C12 alkyl radical;
(ii) $NH(CH_2)_m CO_2H$;
R denotes a radical chosen from saturated or unsaturated $C_2$-$C_{18}$ acyl.

12. The cosmetic process according to claim 11, wherein the compound of formula (I) or a salt thereof, optical isomers, stereoisomers, enantiomers and diastereoisomers thereof or a geometrical isomer thereof is chosen from those for which:
$A_1$ denotes a radical —NH—$(CH_2)_m$—$CO_2H$;
$A_2$ denotes a radical —NH—$(CH_2)_m$—$CO_2H$, or a hydroxyl radical (OH);

$A_3$ denotes a radical $NH_2$;
R denotes an acetyl radical.

13. The cosmetic process according to claim 4, wherein the compound of formula (I) is chosen from the following compounds, or a salt thereof, optical isomers, stereoisomers, enantiomers and diastereoisomers thereof, or geometrical isomers thereof:

Compound 1

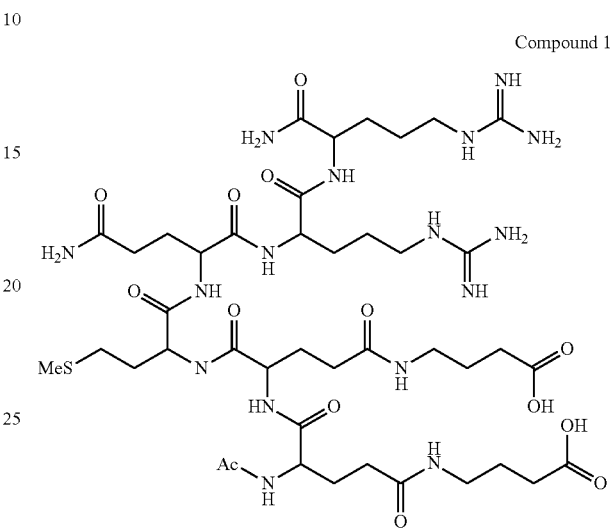

Compound 2

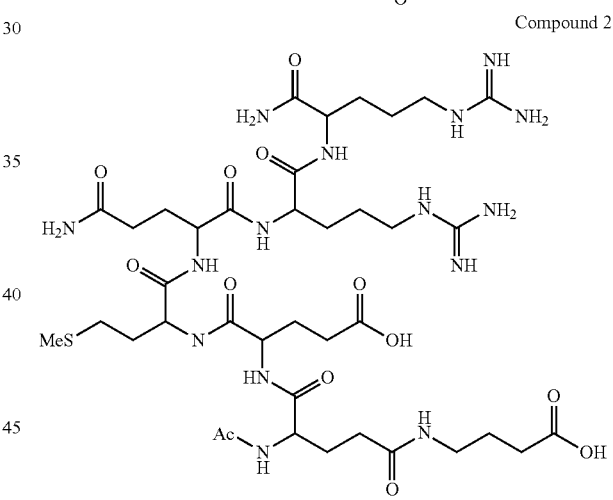

Compound 3

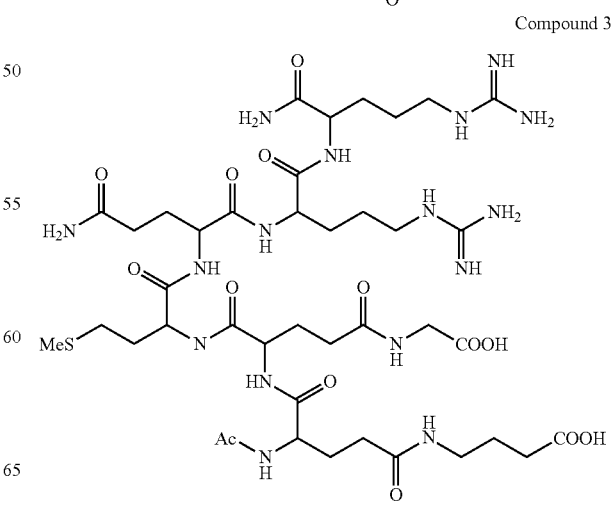

-continued

Compound 4

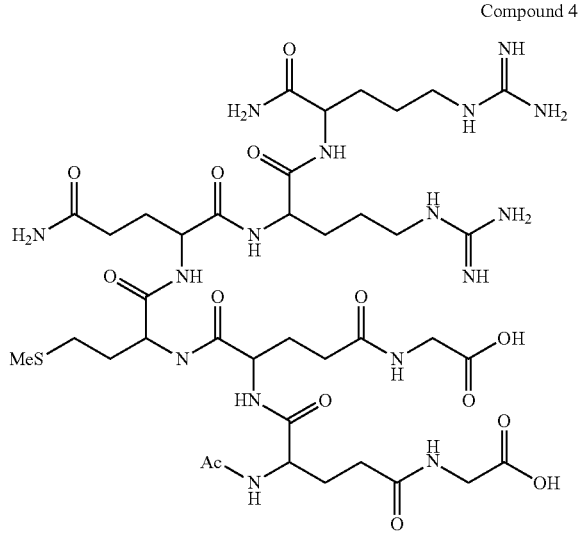

Compound 5

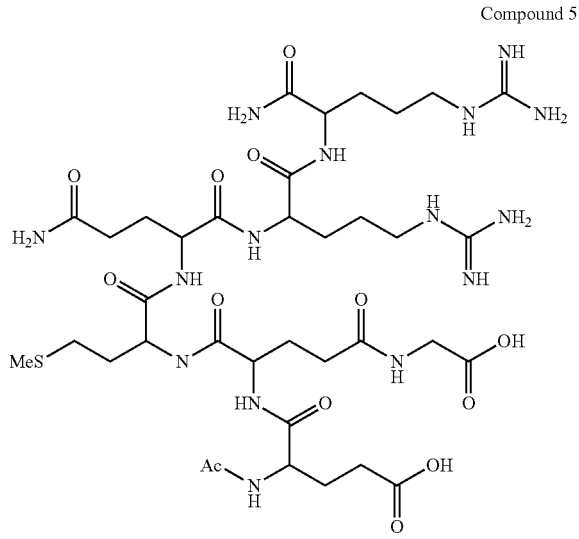

Compound 6

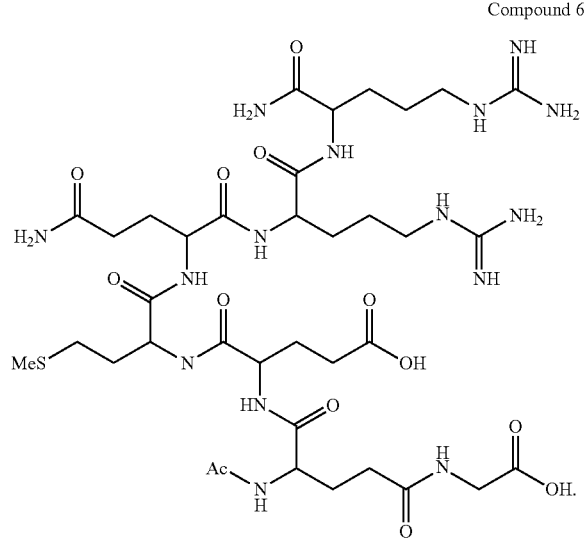

14. The compound according to claim 5 wherein the compound of formula (I) or a salt thereof, optical isomers, stereoisomers, enantiomers and diastereoisomers thereof or a geometrical isomer thereof is chosen from those for which:
   $A_1$ denotes a radical OH.

15. The compound according to claim 14 wherein the compound of formula (I) or a salt thereof, optical isomers, stereoisomers, enantiomers and diastereoisomers thereof or a geometrical isomer thereof is chosen from those for which:
   $A_2$ denotes a radical $—NH(CH_2)_mCO_2H$, and
   $A_3$ denotes a radical chosen from:
   (i) $NR_4R_5$ or
   (ii) $—NH(CH_2)_mCO_2H$ and
   R denotes a radical chosen from:
   1. saturated or unsaturated $C_2$-$C_6$ acyl
   2) linear or branced, saturated or unsaturated $C_1$-$C_{16}$ alkyl
   3) a group of structure:

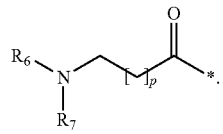

16. The compound according to claim 15, in which the compound of formula (I) or a salt thereof, optical isomers, stereoisomers, enantiomers and diastereoisomers thereof or a geometrical isomer thereof is chosen from those for which:
   R denotes an acetyl radical, $A_3$ denotes a radical $NH_2$, $A_1$ denotes a hydroxyl radical and $A_2$ denotes a radical $—NH—(CH_2)_m—CO_2H$.

17. The compound according to claim 5, in which the compound of formula (I) or a salt thereof, optical isomers, stereoisomers, enantiomers and diastereoisomers thereof or a geometrical isomer thereof is chosen from those for which:
   $A_1$ denotes a radical $—NH—(CH_2)_m—CO_2H$, or a group chosen from

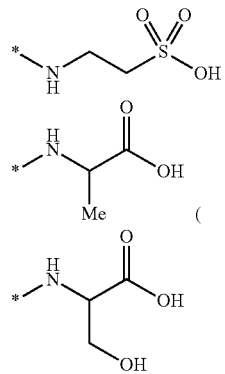

$A_2$ denotes $—OR_3$, a radical $—NH—(CH_2)_m—CO_2H$, or a radical chosen from

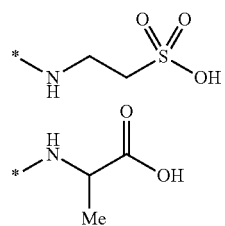

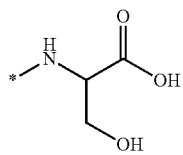

$A_3$ denotes a radical chosen from:
(i) $NR_4R_5$ or
(ii) —NH—$(CH_2)_m$—$CO_2H$
(iii) a radical chosen from

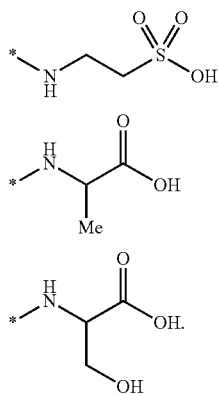

18. The composition according to claim 6, in which the compound of formula (I) or a salt thereof, optical isomers, stereoisomers, enantiomers and diastereoisomers thereof or a geometrical isomer thereof is chosen from those for which:
   $A_1$ denotes a radical —NH—$(CH_2)_m$—$CO_2H$ and
   $A_2$ denotes a radical —NH—$(CH_2)_m$—$CO_2H$, or a OH group
   $A_3$ denotes a group chosen from:
   (i) $NR_4R_5$ with $R_1$ and $R_2$, which may be identical or different, denoting hydrogen or a linear or branched, saturated or unsaturated $C_1$-$C_{12}$ alkyl radical;
   (ii) —NH—$(CH_2)_m$—$CO_2H$;
   R denotes a radical chosen from saturated or unsaturated $C_2$-$C_{18}$ acyl.

19. The compound according to claim 5, in which the compound of formula (I) is chosen from the following compounds, or a salt thereof, optical isomers, stereoisomers, enantiomers and diastereoisomers thereof, or geometrical isomers thereof:

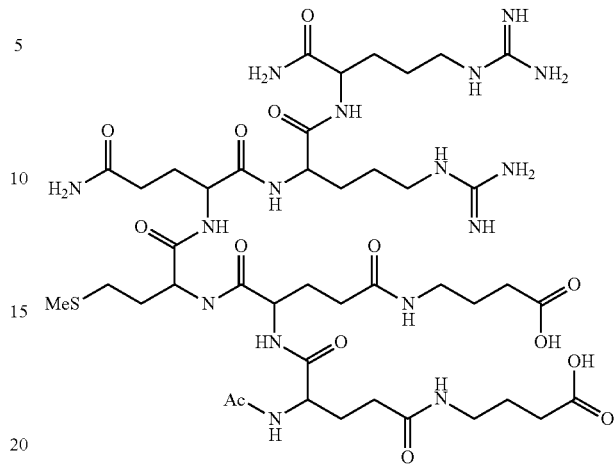

Compound 1

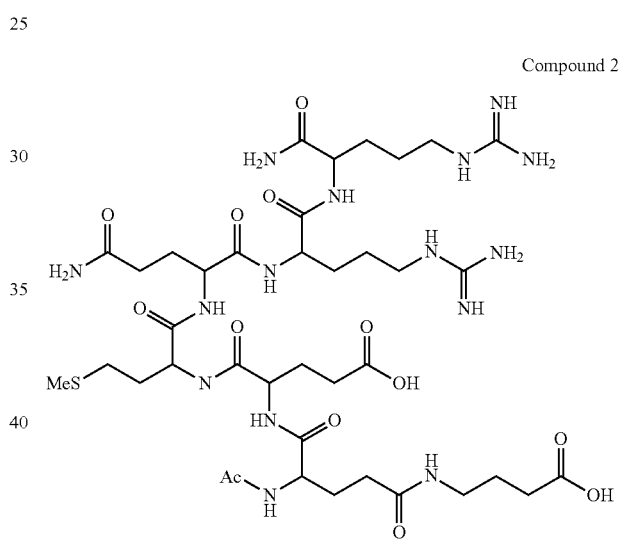

Compound 2

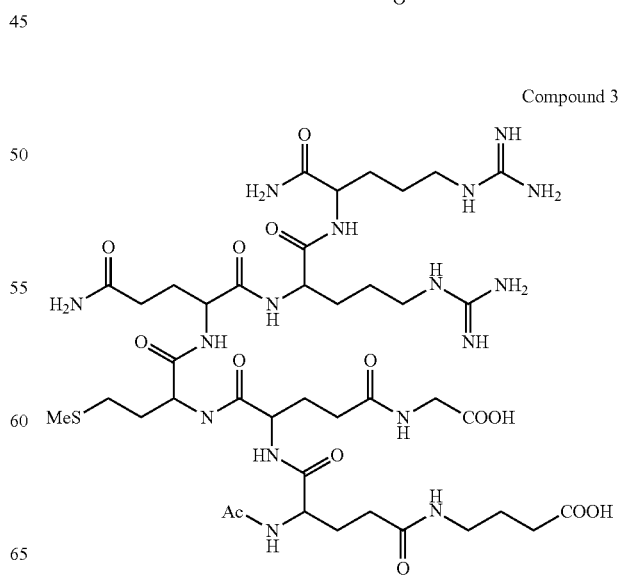

Compound 3

Compound 4

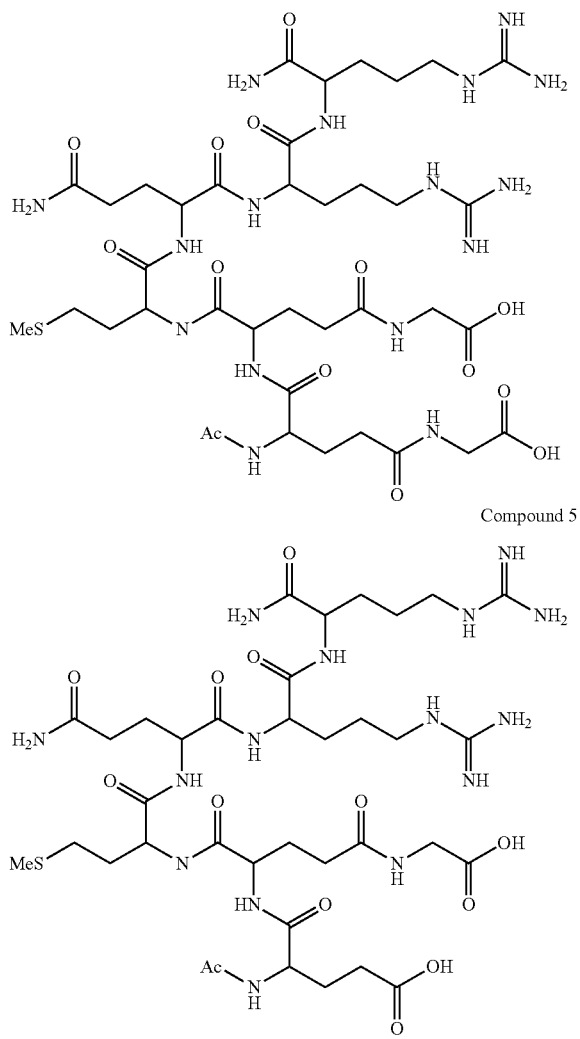

Compound 5

Compound 6

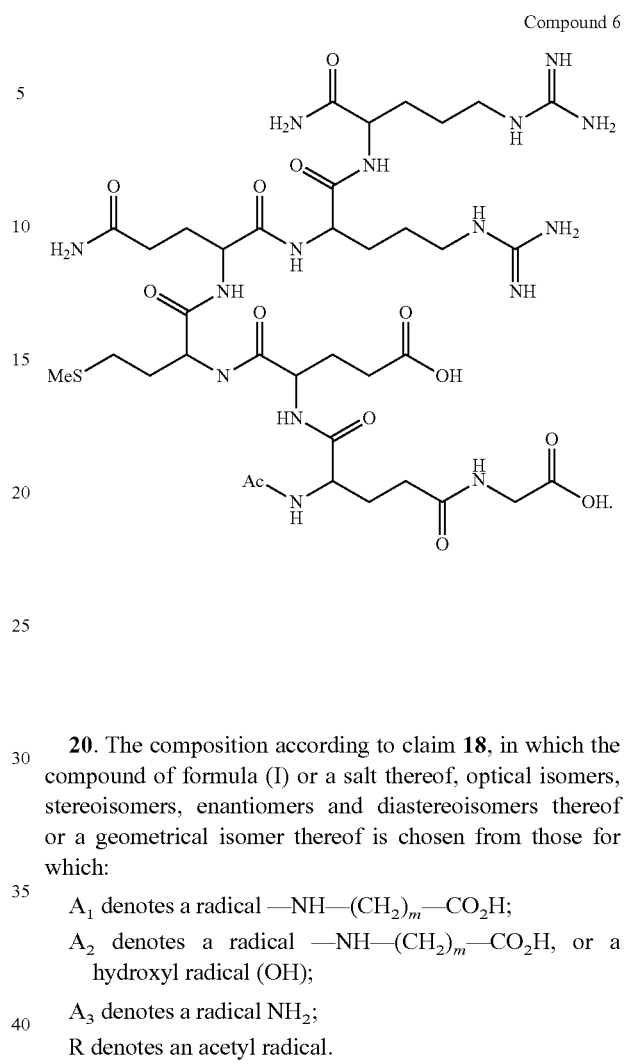

20. The composition according to claim 18, in which the compound of formula (I) or a salt thereof, optical isomers, stereoisomers, enantiomers and diastereoisomers thereof or a geometrical isomer thereof is chosen from those for which:

$A_1$ denotes a radical —NH—$(CH_2)_m$—$CO_2H$;

$A_2$ denotes a radical —NH—$(CH_2)_m$—$CO_2H$, or a hydroxyl radical (OH);

$A_3$ denotes a radical $NH_2$;

R denotes an acetyl radical.

* * * * *